US009889192B2

United States Patent
Dietzschold et al.

(10) Patent No.: US 9,889,192 B2
(45) Date of Patent: Feb. 13, 2018

(54) IMMUNIZATION WITH RABIES VIRUS VECTOR EXPRESSING FOREIGN PROTEIN ANTIGEN

(71) Applicant: THOMAS JEFFERSON UNIVERSITY, Philadelphia, PA (US)

(72) Inventors: Bernhard Dietzschold, Newtown Square, PA (US); Douglas Craig Hooper, Medford, NJ (US); Milosz Faber, Lansdowne, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 0 days.

(21) Appl. No.: 14/430,441

(22) PCT Filed: Sep. 24, 2013

(86) PCT No.: PCT/US2013/061359
§ 371 (c)(1),
(2) Date: Mar. 23, 2015

(87) PCT Pub. No.: WO2014/055289
PCT Pub. Date: Apr. 10, 2014

(65) Prior Publication Data
US 2015/0209422 A1 Jul. 30, 2015

Related U.S. Application Data

(60) Provisional application No. 61/708,197, filed on Oct. 1, 2012.

(51) Int. Cl.
*A61K 39/00* (2006.01)
*A61K 39/155* (2006.01)
*A61K 39/205* (2006.01)
*C12N 7/04* (2006.01)
*A61K 39/12* (2006.01)
*A61K 39/39* (2006.01)
*C07K 14/005* (2006.01)
*C12N 7/00* (2006.01)

(52) U.S. Cl.
CPC ........ *A61K 39/155* (2013.01); *A61K 39/0007* (2013.01); *A61K 39/12* (2013.01); *A61K 39/205* (2013.01); *A61K 39/39* (2013.01); *C07K 14/005* (2013.01); *C12N 7/00* (2013.01); *C12N 7/04* (2013.01); *A61K 2039/5254* (2013.01); *A61K 2039/5256* (2013.01); *A61K 2039/545* (2013.01); *C12N 2760/18034* (2013.01); *C12N 2760/18234* (2013.01); *C12N 2760/20122* (2013.01); *C12N 2760/20134* (2013.01); *C12N 2760/20143* (2013.01)

(58) Field of Classification Search
None
See application file for complete search history.

(56) References Cited

U.S. PATENT DOCUMENTS

| 7,223,584 | B2 | 5/2007 | Dietzschold et al. |
|---|---|---|---|
| 7,695,724 | B2 | 4/2010 | Dietzschold et al. |
| 8,282,939 | B2 | 10/2012 | Faber et al. |
| 2003/0113346 | A1 | 6/2003 | Dietzchold et al. |
| 2008/0274130 | A1 | 11/2008 | Rupprecht et al. |
| 2008/0311147 | A1 | 12/2008 | Schnell et al. |
| 2009/0214428 | A1* | 8/2009 | Dimitrov ........... C07K 16/1027 424/9.1 |
| 2011/0110952 | A1 | 5/2011 | Challita-Eid et al. |

FOREIGN PATENT DOCUMENTS

| RU | 2435857 C2 | 12/2011 |
|---|---|---|
| WO | WO-01/55330 A2 | 8/2001 |
| WO | 2003030933 A1 | 4/2003 |

OTHER PUBLICATIONS

Frey et al., "Temperature Dependence of Cell-Cell Fusion Induced by the Envelope Glycoprotein of Human Immunodeficiency Virus Type 1", *J. Virol.* 69(3):1462-1472 (1995).
Schnell et al., "Recombinant Rabies virus as Potential live-viral Vaccines for HIV-1", *PNAS* 97(7):3544-3549 (Mar. 28, 2000).
Faber et al., "Effective Preexposure and Postexposure Prophylaxis of Rabies with a Highly Attenuated Recombinant Rabies Virus", *PNAS* 106(27):11300-11305 (Jul. 7, 2009).
Lu, "Heterologous Prime-boost Vaccination", *Current Opinion in Immunology* 21:346-351 (2009).
Faber et al., "Dominance of a Nonpathogenic Glycoprotein Gene over a Pathogenic Glycoprotein Gene in Rabies Virus", *J. Virol.*, 81(13) pp. 7041-7047 (Jul. 2007).

(Continued)

*Primary Examiner* — Michelle S Horning
(74) *Attorney, Agent, or Firm* — Cozen O'Connor

(57) ABSTRACT

An immune response in a subject is elicited by a regiment comprising immunization with an attenuated recombinant rabies virus encoding at least one foreign protein antigen, and booster immunization with the at least one foreign protein antigen in a vehicle that does not contain adjuvant. The foreign protein antigen may comprise a prion protein antigen, a cancer-associated antigens, a viral antigen, a bacterial antigens, or a protozoal antigen. The prime/boost regimen produces predominantly IgG 2A/C and IgG 2B antibodies against the foreign protein antigen, indicating a TH1 response. Rabies virus attenuation may be provided, for example, by one or more mutations in the rabies glycoprotein gene which confers attenuation of pathogenicity.

20 Claims, 6 Drawing Sheets

(56) References Cited

OTHER PUBLICATIONS

Faber et al., "A Single Amino Acid Change in Rabies Virus Glycoprotein Increases Virus Spread and Enhances Virus Pathogenicity", *J. Virol.*, 79(22) pp. 14141-14148 (Nov. 2005).

Faber et al., "Overexpression of the Rabies Virus Glycoprotein Results in Enhancement of Apoptosis and Antiviral Immune Response", *J. Virol.*, 76(7) pp. 3374-3381 (Apr. 2002).

Schnell et al., "Infectious Rabies Viruses From Cloned cDNA", *EMBO Journal*, 13(18): pp. 4195-4203 (1994).

PMID:1768463, abstracting Hu et al., "Neutralizing Antibodies Against HIV-1 BRU and SF2 Isolates Generated in Mice Immunized with Recombinant Vaccinia Virus Expressing HIV-1 (BRU) Envelope Glycoproteins and Boosted with Homologous gp160", *AIDS Res Hum Retroviruses*, vol. 7, pp. 615-620, Jul. 1991 (Abstract only).

PMID:1531159, abstracting Hu et al., "Protection of Macaques Against SIV Infection by Subunit of SIV envelope Glycoprotein gp160", *Science*, vol. 255, pp. 456-459, Jan. 24, 1992 (Abstract only).

PMID:3162762, abstracting Zagury et al., "A Group Specific Anamnestic Immune Reaction Against HIV-1 induced by a Candidate Vaccine Against AIDS", *Nature*, vol. 332, p. 728-731, Apr. 21, 1988 (Abstract only).

International Search Report and Written Opinion for PCT/US13/61359 dated Dec. 9, 2013.

Kgaladi, J.; Faber, M.; Dietzschold, B.; Nel, L.H.; Markotter, W. "Pathogenicity and Immunogenicity of Recombinant Rabies Viruses Expressing the Lagos Bat Virus Matrix and Glycoprotein: Perspectives for a Pan-Lyssavirus Vaccine". Trop. Med. Infect. Dis. 2017, 2, 37.

Faul, E.J., et al., "Rabies virus-based vaccines elicit neutralizing antibodies, polyfunctional CD8+ T cell, and protect rhesus macaques from AIDSlike disease after SIVmac251 challente", Vaccine, vol. 28, No. 2, pp. 299-308, 2009.

\* cited by examiner

IMMUNIZATION WITH RABIES VIRUS VECTOR EXPRESSING FOREIGN PROTEIN ANTIGEN

CROSS-REFERENCE TO RELATED APPLICATION

The benefit of the filing date of U.S. Provisional Patent Application No. 61/708,197, filed Oct. 1, 2012, is hereby claimed. The entire disclosure of the aforesaid application is incorporated herein by reference.

REFERENCE TO GOVERNMENT GRANT

The invention described herein was made with government support under grant no. R21AI068837-01A2 awarded by the National Institutes of Health. The government has certain rights in this invention.

SEQUENCE LISTING

The instant application contains a Sequence Listing which has been submitted in ASCII format via EFS-Web and is hereby incorporated by reference in its entirety. Said ASCII copy, created on Jun. 17, 2013, is named 37075_0280_00_WO_SeqListing_ST25, and is 3,396 bytes in size.

FIELD OF THE INVENTION

The invention relates to the field of biotechnology and immunology, and in particular to the utilization of recombinant rabies virus vaccines expressing foreign antigens, for immunization against those foreign antigens.

BACKGROUND OF THE INVENTION

Rabies virus (RV) is a non-segmented negative-strand RNA virus within the Rhabdoviridae family and lyssavirus genera. The RV genome is about 12-kb in size and encodes five monocistronic RNAs encoding the nucleocapsid protein (N), phosphoprotein (P), matrix protein (M), the transmembrane glycoprotein (G), and the viral polymerase (L). The RV N protein encapsidates the viral RNA to form the ribonucleoprotein (RNP), which is the template for RNA transcription and replication by the viral polymerase-complex composed of the P and L proteins. The RV M bridges the RNP with the cytoplasmic domain (CD) of RV G in the host cell-derived viral membrane. The RV G mediates infection of the host cell. The main feature of rabies virus is neuroinvasiveness, which refers to its unique ability to invade the central nervous system (CNS) from peripheral sites.

Rabies virus is a promising vaccine vector able to induce humoral and cellular immune responses efficiently to foreign antigens. Recombinant live-viral vectors expressing foreign antigens efficiently induce potent cellular and humoral immune responses against the expressed antigens. Because of low seroprevalence in the human population, RV is an excellent viral vector candidate. Methods for engineering the virus are well established, up to two foreign genes totaling 6.5 kb have been incorporated thus far, and foreign sequences are stably maintained. RV grows to high titers in cell lines approved for human vaccine production and manufacture is economical. See, Smith et al., 2006, *Virology*, 353(2): 344-356. For example, replication-competent RV comprising heterologous nucleic acids sequences encoding the HIV-1 gp160 is described in WO 01/55330. Immunization with RV encoding bacterial, viral or cancer antigens, fused to at least a portion of the RV N protein or G protein is described in US Pat. Pub. 2008/0311147. Expression of HIV-1 Env or Gag results in potent immune responses directed against HIV-1 (Schnell et al, 2000, *Proc. Natl. Acad. Sci USA* 97(7): 3544-3549).

The availability of reverse genetics technology, has allowed the modification of RV viral elements that account for pathogenicity and immunogenicity, and has made the systematic development of safer and more potent modified-live rabies vector feasible. For example, the pathogenicity of fixed RV strains (i.e., ERA, SAD) can be completely abolished for immunocompetent mice by introducing single amino acid exchanges in their G protein (Faber et al., 2005, *J Virol* 79:14141-14148). RVs containing a SADB19 G with an $Arg_{333} \rightarrow Glu_{333}$ mutation are nonpathogenic for adult mice after intracranial/intracerebral inoculation; an $Asn_{194} \rightarrow Ser_{194}$ mutation in the same gene prevents the reversion to pathogenic phenotype (Faber et al., 2005, *J Virol* 79:14141-14148; Dietzschold et al., 2004, *Vaccine* 23:518-524; U.S. Pat. No. 7,695,724). The G gene containing both mutations has been designated as "GAS". Using the GAS gene, the single and double GAS RV variants, SPBN-GAS and SPBNGAS-GAS, respectively, were constructed (Faber et al., 2005, *J Virol* 79:14141-14148; Li et al., 2008, *Vaccine* 26:419-426). The introduction of a second G gene significantly improves the efficacy of the vaccine by enhancing its immunogenicity through higher expression of G (Faber et al., 2002, *J Virol* 76:3374-3381). Elevated G expression is associated with the strong up-regulation of genes related to the NFκB signaling pathway, including IFN-α/β and IFN-γ (Li et al., 2008, *Vaccine* 26:419-426) and increased cell death (Faber et al., 2002, *J Virol* 76:3374-3381). Furthermore, the presence of two G genes also decreases substantially the probability of reversion to pathogenicity because the nonpathogenic phenotype determined by GAS is dominant over a pathogenic G that could emerge during virus growth in vivo or in vitro (Faber et al., 2007, *J Virol* 81:7041-7047).

A further improvement in recombinant RV safety is the highly attenuated triple RV G variant, SPBAANGAS-GAS-GAS (Faber et al., 2009, *Proc. Natl. Acad. Sci USA* 206 (27):11300-11305). The SPBAANGAS-GAS-GAS variant is completely nonpathogenic after intracranial infection of mice that are either developmentally immunocompromised (e.g., 5-day-old mice) or mice that have inherited deficits in immune function.

Recombinant RVs that express foreign antigens derived from various disease-causing agents may serve as useful vaccine vectors. However, a problem that often arises with the use of recombinant viruses in vaccinology is that they are designed such that the immune system is exposed to antigens of the virus vector and foreign agent coincidentally, and the immune response against the virus vector dominates over the response to the foreign antigen.

Adjuvants have been expensively used to improve the potency of vaccines. Safety and tolerability are critical regulatory issues confronting adjuvant use. The field of adjuvant development is reviewed by Petrovsky et al., "New-Age Vaccine Adjuvants: Friend or Foe?" *BioPharm International*, Aug. 2, 2007, http<colon>//biopharminternational<dot>findpharma<dot>com/biopharm/article/articleDetail<dot>jsp?id=444996&sk=&date=&pageID=5.

As described by Petrovsky et al., the benefits of incorporating any adjuvant into vaccines must be balanced against any increased reactogenicity or risk of adverse reactions. In most cases, increased adjuvant potency is associated with increased reactogenicity and toxicity. For example, while complete Freund's adjuvant (CFA) is the "gold standard" in terms of adjuvant potency, its extreme reactogenicity and toxicity precludes its use in human vaccines.

As described by Petrovsky et al., a major unsolved challenge in adjuvant development is how to achieve a potent adjuvant effect while avoiding reactogenicity or toxicity. Most newer human adjuvants including MF59,4 ISCOMS,5 QS21,6 AS02,7 and ASO48 have substantially higher local reactogenicity and systemic toxicity than alum. Even alum, despite being FDA-approved, has significant adverse effects including injection site pain, inflammation, and lymphadenopathy, and less commonly injection-site necrosis, granulomas, or sterile abscess. Although many adjuvant-caused vaccine reactions are not life-threatening and do resolve over time, they remain one of the most important barriers to better community acceptance of routine prophylactic vaccination. This particularly applies to pediatric vaccination where prolonged distress in the child due to increased reactogenicity may lead directly to parental and community resistance to vaccination.

Use of oil-in-water emulsions has been limited by their reactogenicity and potential for adverse reactions. Oil-in-water particles are irritants and cause local inflammation, inducing a chemotactic signal that elicits local macrophage invasion. Because of frequent adverse reactions, the major human use of oil-in-water emulsions has been in therapeutic cancer and HIV vaccines. Petrovsky et al., supra. Other adjuvants proposed for human use are characterized b varying degrees of safety concerns and/or reactogenicity risks: monophosphoryl Lipid A (significant reactogenicity); unmethylated CpG dinucleotide (overall, reactogenicity, toxicity, including site reactions, flu-like symptoms, and headache), QS21, comprising triterpenoid glycosides (saponins) derived from the bark of the South American soap bark tree (severe injection site pain, granulomas, and severe hemolysis); ISCOMs, which are immunostimulating complexes containing a saponin, a sterol, and, optionally, a phospholipid (toxicity, and safety concerns). Petrovsky et al., supra. Only recently, a nanocrystalline particles of inulin, Advax, has shown promising freedom from side effects, the adjuvant is a natural plant-derived polysaccharide consisting of a chain of fructose molecules ending in a single glucose.

What are needed are recombinant RV-based compositions and immunization methods that provide for a vigorous immune response to foreign antigens expressed by the recombinant RVs, without the use of adjuvants.

SUMMARY OF THE INVENTION

A method of eliciting an immune response in a subject comprises the steps of: (a) providing an attenuated recombinant rabies virus encoding at least one foreign protein antigen operably linked to control sequences which directs the expression of said foreign antigen in a suitable recipient cell; (b) introducing said rabies virus into a recipient cell of said subject under conditions that permit the expression of said one or more foreign protein antigens, thereby eliciting an immune response to said foreign protein antigen; and (c) boosting said immune response to said foreign protein antigen by administering to said subject said foreign protein antigen contained in a booster composition which is adjuvant-free.

The foreign protein antigen may comprise, for example, a prion protein antigen, a cancer-associated antigen, a viral antigen, a bacterial antigen, or a protozoal antigen.

The rabies virus is attenuated, i.e., rendered non-pathogenic, for example by introducing one or more mutations in the rabies glycoprotein (G) gene which confers attenuation. For example, the attenuated recombinant rabies virus may comprise a mutated G gene that encodes a rabies virus glycoprotein wherein the amino acid 333 is glutamic acid. The mutated G gene may further encodes a rabies virus glycoprotein wherein the amino acid 194 is other than lysine, e.g. amino acid 194 is serine. In some embodiments, the attenuated recombinant rabies virus comprises two or more G genes. At least one, and preferably all, of the G genes comprise a pathogenicity-attenuating mutation.

In some embodiments, a nucleotide sequence encoding the at least one foreign protein antigen is located between two G genes in the genome of said attenuated recombinant rabies virus. In other embodiments, a nucleotide sequence encoding the at least one foreign protein antigen is located between the M and L genes in the genome of the attenuated recombinant rabies virus.

In certain embodiments, immunization with the attenuated recombinant rabies virus encoding at least one foreign protein occurs without adjuvant.

Also provided is a kit for practicing the aforementioned immunization regimen. The kit may comprise: (a) first composition comprising an attenuated recombinant rabies virus encoding at least one foreign protein antigen operably linked to control sequences which directs the expression of said foreign antigen in a suitable recipient cell; and (b) a second composition comprising the at least one foreign protein antigen, wherein said second composition is adjuvant-free. In some embodiments, the first composition of the kit is also adjuvant-free.

DESCRIPTION OF THE FIGURES

FIG. 3 are graphs of the production of NiV neutralizing antibodies (panel A) the production of NiV G protein binding antibodies (panel B). Mice were first immunized with $10^5$ FFU of the RV variant SPBNGAS-GAS. Then 29 days later one group received a booster immunization with $10^5$ FFU SPBAANGAS-NG-GAS (bars marked SPBN-GAS-GAS/SPAANGAS-NG-GAS) while the other group was immunized again with $10^5$ FFU SPBN (bars marked SPBNGAS-GAS/SPBNGAS-GAS). The mice were bled at 21 days after the primary immunization (1st Bleed: left bars in each of the two bar sets in the panels) and 10 days after the booster immunization (2nd Bleed: Right bars in each of the two bar sets in the panels). NiV neutralization titers were determined using pooled serum. The results are shown in FIG. 3A (NiV neutralizing antibodies) and FIG. 3B (NiV-G binding antibodies). The bars marked NiV-G-binding titers are presented as mean values±standard error.

FIG. 4 is a graph of the production of anti-NiV-G antibodies. Two groups of mice were first immunized with $10^5$ FFU SPBAANGAS-NG-GAS or $10^5$ FFU of the RV variant SPBNGAS-GAS. Twenty three days later, both groups of mice received a booster immunization with recombinant-expressed soluble adjuvant-free NiV-G. The mice were bled at 19 days after the primary immunization (left-hand bars in each bar pair in FIG. 4) and 10 days after the booster immunization (right-hand bars in each bar pair) and NiV-G-binding antibodies were measured. NiV-G-binding titers are presented as mean values±standard error.

FIG. 5 comprises an immunization and bleed timeline A, and a series of graphs B-D showing the production of anti-NiV-G antibodies. Mice were immunized on day zero and day 29 with $10^5$ FFU SPBAANGAS-NG-GAS. One hundred ninety-five days after the second immunization, the mice received a booster immunization with recombinant-expressed soluble NiV-G. The mice were bled at the bleed times shown in the timeline marked A. NiV-neutralizing antibodies (panel B), whole anti-NiV-G-specific antibodies (panel C), and NG-specific IgM, IgG 1, IgG 2A, and IgG 2B isotypes (panel D) were measured. NiV neutralization titers were determined using pooled serum. NiV-G-binding titers are presented as mean values±standard error.

FIGS. 6A and 6B show production of anti-NiV-G antibodies. Mice were immunized with NiV-G and 3 weeks later received a booster immunization with NiV-G. The mice were bled at 10 days after the primary immunization and 10 days after the booster immunization. Total NiV-G binding antibodies were measured for the two bleeds (FIG. 6A). NiV-G-specific IgM, IgG 1, IgG 2A, and IgG 2B isotypes produced after booster immunization were measured using an ELISA (FIG. 6B). NiV-G-binding titers are presented as mean values±standard error.

DEFINITIONS

The definitions used in this application are for illustrative purposes and do not limit the scope of the invention.

The articles "a" and "an" are used herein to refer to one or to more than one (e.g., to at least one) of the grammatical object of the article. By way of example, "an element" means one element or more than one element.

The term "about" will be understood by persons of ordinary skill in the art and will vary to some extent depending on the context in which it is used. As used herein, "about" is meant to encompass variations of ±20% or ±10%, more preferably ±5%, even more preferably ±1%, and still more preferably ±0.1%.

The term "antibody," as used herein, refers to an immunoglobulin molecule which is able to specifically bind to a specific epitope on an antigen. Antibodies can be intact immunoglobulins derived from natural sources or from recombinant sources and can be immunoreactive portions of intact immunoglobulins. Antibodies are typically tetramers of immunoglobulin molecules. The antibodies that may be used in the practice of the present invention may exist in a variety of forms including, for example, polyclonal antibodies, monoclonal antibodies, Fv, Fab and F(ab)2, as well as single chain antibodies and humanized antibodies (Harlow et al., 1999, Using Antibodies: A Laboratory Manual, Cold Spring Harbor Laboratory Press, New York; Harlow et al., 1989, Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology*, Second Ed., 1984, Benjamin/Cummings: Menlo Park, Calif., p. 384). Adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvants such as BCG (bacille Calmette-Guerin) and *Corynebacterium parvum*. The term "adjuvant-free" refers to any preparation which does not contain an adjuvant, as described above.

As used herein, each "amino acid" is represented by the full name thereof, by the three letter code corresponding thereto, or by the one-letter code corresponding thereto, as indicated in the following table:

| Full Name | Three-Letter Code | One-Letter Code |
|---|---|---|
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

The expression "amino acid" as used herein is meant to include both natural and synthetic amino acids, and both D and L amino acids.

The term "animal" has its ordinary meaning, and is meant to include human beings.

"Attenuated" as used herein in the context of a live virus, such as a rabies virus, means that the ability for the virus to infect a cell or subject and/or its ability to produce disease is reduced (for example, eliminated). Attenuation may arise from either a genetic mechanism involving premature termination of transcription from the RV genome, or immunologically as a process whereby a pathogenic RV loses its virulence.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Figure 1:
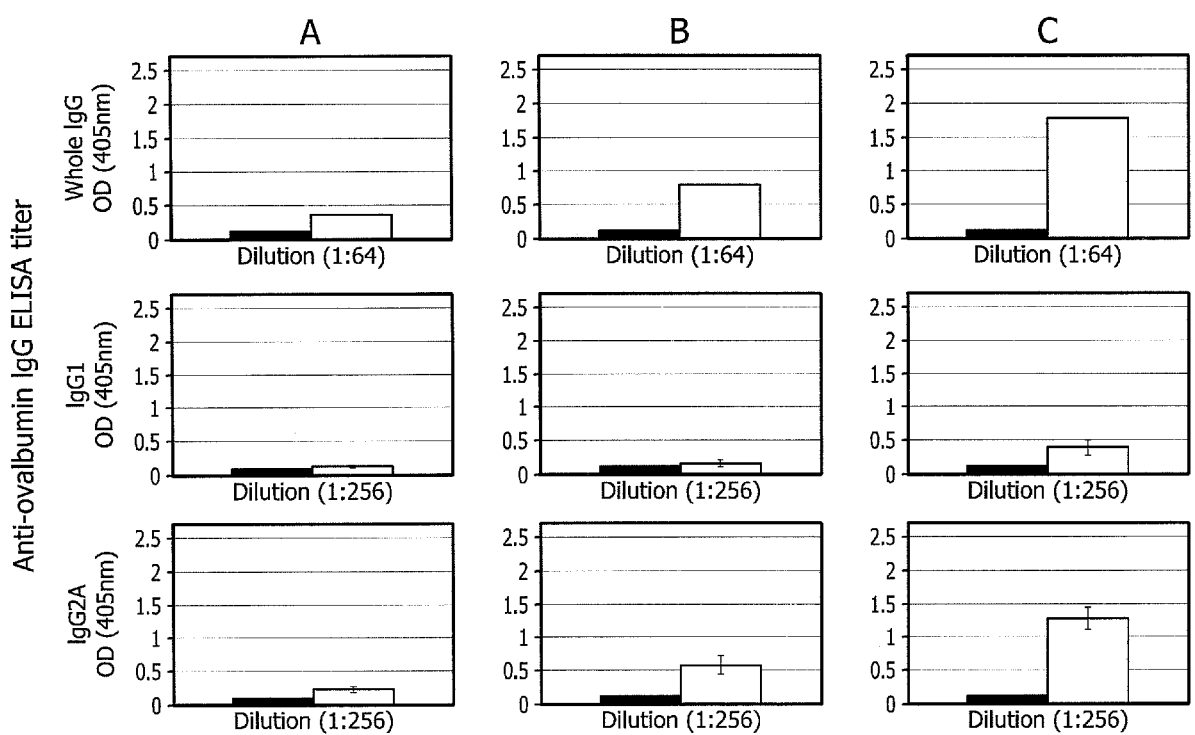
FIG. 1 is a series of graphs showing ovalbumin antibody titers for total immunoglobulin, (Whole IgG), IgG1 and IgG2A in mice immunized with SPBAANGAS-OVA-GAS or SPBAAGAS-GAS (column A), followed by booster immunization with SPBAANGAS-OVA-GAS (column B) and third immunization with soluble OVA (column C). In each box, the left-hand bar represents mice initially immunized with SPBAAGAS-GAS, while the right-hand bar represents mice initially immunized with SPBAAGAS-OVA-GAS.

"Gene expression" or "expression" as used herein refers to the process by which information from a gene is made into a functional gene product, such as RNA or protein. Thus, the "level of expression" of a gene product of a marker gene of the, in a sample of interest, refers to the level of RNA, particularly the level of mRNA, or the level of the encoded protein, and is not intended to be limited to either.

As used herein, an "expression vector" is a genetic element that functions as an autonomous unit of DNA replication under its own control sequence, to which another DNA segment may be attached or inserted so as to bring about replication of the attached or inserted segment. Expression vectors include plasmids, phages or cosmids. In general, expression vectors contain promoter sequences which facilitate the efficient transcription and translation of the attached or inserted DNA segment in a particular host cell. The expression vector also typically contains an origin of replication and transcription terminator(s), as well as specific genes which are capable of providing phenotypic selection in transfected host cells By a "foreign protein antigen" or expressed by a recombinant rabies virus is meant an antigen of a protein that is not native to the rabies virus expressing the antigen. In certain embodiments where the foreign antigen is an antigen of a virus, the virus is other than a rabies virus.

As used herein, the term "gene" refers to an element or combination of elements that are capable of being expressed in a cell, either alone or in combination with other elements. In general, a gene comprises (from the 5' to the 3' end): (1) a promoter region, which includes a 5' nontranslated leader sequence capable of functioning in any cell such as a prokaryotic cell, a virus, or a eukaryotic cell (including transgenic animals); (2) a structural gene or polynucleotide sequence, which codes for the desired protein; and (3) a 3' nontranslated region, which typically causes the termination of transcription and the polyadenylation of the 3' region of the RNA sequence. Each of these elements is operably linked by sequential attachment to the adjacent element.

As used herein, "gene products" include any product that is produced in the course of the transcription, reverse-transcription, polymerization, translation, post-translation and/or expression of a gene. Gene products include, but are not limited to, proteins, polypeptides, peptides, peptide fragments, or polynucleotide molecules.

As used herein, "RV G protein gene" or "G protein gene" or "G gene" means the nucleic acid sequences which, when present in an RV genome, are sufficient to encode an RV glycoprotein in an infected cell. The G protein gene thus includes a coding sequence which is flanked on the 3' end with a short transcriptional start sequence, and on the 5' end with a short transcriptional stop/polyadenylation sequence. The G gene can include an intergenic region of 1-59 untranslated nucleotides, which is located between the 5' stop/polyadenylation sequence and the 3' transcriptional start sequence of the next viral gene. See, e.g., pgs. 134-136 of Conzelman K-K (1998), *Ann. Rev. Genet.* 32: 123-62, "Homologous" as used herein, refers to the subunit sequence similarity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous. By way of example, the DNA sequences 3'ATTGCC5' and 5'TATGGC3' are 50% homologous.

As used herein, "homology" is used synonymously with "identity."

The term "immunization" refers to a process to induce partial or complete protection against a disease. Alternatively, the term refers to a process to induce or amplify an immune system response to an antigen.

An "immune response" to an antigen or vaccine composition is the development in a subject of a humoral and/or a cell-mediated immune response to molecules present in the antigen or vaccine composition of interest. For purposes of the present invention, a "humoral immune response" is an antibody-mediated immune response and involves the generation of antibodies with affinity for the antigen/vaccine of the invention, while a "cell-mediated immune response" is one mediated by T-lymphocytes and/or other white blood cells. A "cell-mediated immune response" is elicited by the presentation of antigenic epitopes in association with Class I or Class II molecules of the major histocompatability complex (MHC).

"Isolated" means altered or removed from the natural state through the actions of a human being. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

A "mutation," as used herein, refers to a change in nucleic acid or polypeptide sequence relative to a reference sequence (which is preferably a naturally-occurring normal or "wild-type" sequence), and includes translocations, deletions, insertions, and substitutions/point mutations. A "mutant," as used herein, refers to either a nucleic acid or protein comprising a mutation.

A "nucleic acid" refers to a polynucleotide and includes poly-ribonucleotides and poly-deoxyribonucleotides.

A coding sequence is "operably linked" to a control sequence such as transcriptional and translational control sequence in a cell when RNA polymerase transcribes the coding sequence into mRNA, which is then trans-RNA spliced and translated into the protein encoded by the coding sequence.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids which can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptide, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "polynucleotide" includes cDNA, RNA, DNA/RNA hybrid, anti-sense RNA, ribozyme, genomic DNA, synthetic forms, and mixed polymers, both sense and antisense strands, and may be chemically or biochemically modified to contain non-natural or derivatized, synthetic, or semi-synthetic nucleotide bases. Also, included within the scope of the invention are alterations of a wild type or synthetic gene, including but not limited to deletion, insertion, substitution of one or more nucleotides, or fusion to other polynucleotide sequences, provided that such changes in the primary sequence of the gene do not alter the expressed peptide ability to elicit passive immunity.

"Pharmaceutically acceptable" means physiologically tolerable, for either human or veterinary applications.

As used herein, "pharmaceutical compositions" include formulations for human and veterinary use.

As used herein, "promoter" refers to a region of a DNA sequence active in the initiation and regulation of the expression of a structural gene. This sequence of DNA, usually upstream to the coding sequence of a structural gene, controls the expression of the coding region by providing the recognition for RNA polymerase and/or other elements required for transcription to start at the correct site.

As used herein, the term "subject" refers to any vertebrate animal, including, but not limited to humans and other primates, rodents (e.g., mice, rats, and guinea pigs), lagamorphs (e.g., rabbits), bovines (e.g., cattle), ovines (e.g., sheep), caprines (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.), as well as feral or wild animals, including, but not limited to, such animals as ungulates (e.g., deer), bear, fish, lagamorphs, rodents, birds, etc.

As used herein, a "transfected" cell is one into which an exogenous or heterologous nucleic acid sequence has been introduced. The nucleic acid sequence which has been introduced can be integrated into the genome of the transfected cell, or can be maintained episomally. A stably transfected cell is one in which the introduced DNA has integrated into a chromosome so that it is inherited by daughter cells through chromosome replication.

The term "vaccine" as used herein is defined as a material used to provoke an immune response after administration of the material to a vertebrate, typically a mammal. In preferred embodiments a vaccine can be an immunogenic composition providing or aiding in prevention of disease. In other embodiments, a vaccine is a composition that can provide or aid in a cure of a disease. In others, a vaccine composition can provide or aid in amelioration of a disease. Further embodiments of a vaccine immunogenic composition can be used as therapeutic and/or prophylactic agents.

A "vector," as used herein, refers to a replicon, such as plasmid, phage or cosmid, to which another DNA segment may be attached so as to bring about the replication of the attached segment.

The term "virus" as used herein is defined as a particle consisting of nucleic acid (RNA or DNA) enclosed in a protein coat, with or without an outer lipid envelope, which is capable of replicating within a whole cell.

As envisioned in the present invention with respect to the disclosed compositions of matter and methods, in one aspect the embodiments of the invention comprise the components and/or steps disclosed herein. In another aspect, the embodiments of the invention consist essentially of the components and/or steps disclosed herein. In yet another aspect, the embodiments of the invention consist of the components and/or steps disclosed herein.

DETAILED DESCRIPTION OF THE INVENTION

A problem that often arises with the use of recombinant viruses in vaccinology for vaccination against foreign antigens, including recombinant RVs expressing foreign antigens, is that the immune response against the virus vector dominates over the response to the foreign antigen. To enhance the immune response to the foreign antigen, a prime/boost immunization regimen is provided. The regimen utilizes live, attenuated, preferably non-pathogenic recombinant RVs expressing one or more foreign protein antigens. In an embodiment, the foreign protein antigen is not expressed in the structure of the recombinant RV but is only expressed in cells infected by the virus. The regimen includes a primary immunization with a highly attenuated recombinant rabies virus vaccine, e.g., SPBAANGAS-GAS, that expresses a particular protein antigen foreign to the rabies virus, and a booster immunization with the corresponding foreign protein antigen in free form, e.g., soluble form. The regimen may include multiple immunizations with the foreign protein antigen-expressing RV, and/or multiple booster immunizations with the foreign protein antigen. The formulation of the booster composition does not contain adjuvant.

Primary immunization with a recombinant RV expressing a foreign protein antigen alone induces a long-lasting T cell memory to the foreign protein antigen. However, the antibody response to foreign antigen is weak after primary immunization with the recombinant RV vaccine and is increased only slightly by secondary administration of the same recombinant RV vaccine. By contrast, booster immunization with the corresponding free foreign protein antigen results in a strong increase in the production of antibodies specific for the foreign protein antigen, surprisingly in the absence of adjuvant in the booster immunization formulation. The magnitude and quality of the immune response that is induced using the recombinant RV-prime immunization followed by adjuvant-free foreign protein antigen boost is superior to that of prime/boost immunization with only a single form of the antigen or other prime-boost strategies (e.g. DNA, then protein).

Notably, predominantly IgG 2A/C and IgG 2B antibodies are produced against the foreign protein after prime/boost immunization with recombinant RV vaccine and soluble antigen, indicating a TH1 response. Importantly, pathological inflammatory mechanisms are not induced by this regimen. On the other hand, prime/boost immunization using soluble proteins only results in the production of relatively low amounts of antigen-specific antibodies which are almost exclusively of the IgG 1 isotype indicating a TH2 response. A TH1 T cell response is generally regarded to have benefits in the defense against certain pathogens and neoplastic cells over a TH2 response. This is particularly true for infections/cancers in tissues that require immune cell infiltration for therapy. Thus, the prime/boost regimen using a recombinant RV vaccine together with the corresponding soluble foreign protein induces an immune response and immunological memory appropriate for optimal protection against a variety of infectious agents.

The live-attenuated recombinant RV delivers a de novo synthesized foreign protein antigen to safely prime an immune response to the protein with the appropriate characteristics, e.g., a TH1 response in the absence of inflammation. The booster immunization with the corresponding soluble foreign protein stimulates primed B and T cells in the vaccinated host to produce a strong TH1 antibody response to the protein. While proteins are useful as antigens because their precise chemical definition allows one to specify the exact epitopes against which an immune response is to be raised, soluble proteins may themselves may be poorly immunogenic, requiring coadministration with strong adjuvants, e.g., Freunds adjuvant. Surprisingly, a strong response is achieved using a booster formulation that does not include adjuvant.

Prime immunization with a recombinant RV vaccine expressing a foreign protein in target infected cells, followed by booster immunization with the corresponding soluble foreign protein, even in the absence of adjuvant in the booster formulation, induces an immune response and immunological memory appropriate for optimal protection against a variety of infectious agents. In the case of immunization against a pathogen, the elicited immune response may comprise a "protective" immune response which serves to protect the subject from an infection. The protection provided need not be absolute, i.e., the infection need not be totally prevented or eradicated, if there is a statistically significant improvement compared with a control population of mammals. Protection may be limited to mitigating the severity or rapidity of onset of symptoms of the infection.

Surprisingly, the invention provides for induction of immunity against antigens that are weakly immunogenic, as is the case for viruses that mediate certain acute and chronic virus infections, as well as antigens expressed by different cancer cells. The invention thus satisfies the need for vaccines that are effective in preventing or curing emerging infectious diseases and cancers. Importantly, pathological inflammatory mechanisms are not induced by the immunization/boost regimen of the present invention.

The RV for use in the practice of the present invention is suitably attenuated. Embodiments of RVs for use in the present invention comprise recombinant non-pathogenic, live rabies viruses that have been modified to prevent or eliminate mutation or reversion to a pathogenic form. In some embodiments, a non-pathogenic recombinant RV comprises a modified or altered G gene. In certain embodiments, attenuation is achieved by one or more mutations in the RV G gene that codes for a glycoprotein. The amino acid(s) in the G protein of a live rabies virus that result in a pathogenic form of the virus can be determined and the G gene, or more specifically the codon(s) for the one or more amino acids in the G gene, can be modified by exchange of one or more nucleotides. The modified G gene provides for a non-pathogenic live rabies virus that eliminates or resists subsequent mutation resulting in a change of amino acids in the expressed glycoprotein from occurring.

Methods for modifying G protein sequences to produce viral attenuation are known and summarized in U.S. Pat. No. 7,223,584. For example, the pathogenicity of a particular rabies virus is related to a G protein determinant that interacts with putative cell surface receptors (Coulon et al. (1982), *J Gen. Virol.* 61: 97; Coulon et al. (1983), *J. Gen. Virol.* 64: 693-696; and Dietzschold et al. (1983), *Proc. Natl. Acad. Sci USA*. Alteration of this G protein determinant can attenuate pathogenicity of the RV. In particular, substitution of arginine at position 333 of the G protein with glutamine or glycine results in a slowdown of virus uptake and a complete loss of pathogenicity of certain RV strains (e.g., ERA, CVS-11). See Dietzschold et al. (1983), supra and Dietzschold et al. (1985), *J. Virol.* 56:12-18.

Deletions or other alterations within the G protein cytoplasmic domain, such that the cytoplasmic tail of the G protein no longer binds to the RNP-M complex, will also attenuate the pathogenicity of an RV strain. For example, replacing the cytoplasmic domain of a particular G protein with that from another RV strain will render the RV apathogenic when administered i.m. See Morimoto et al. (2000), *J. Neuro Virol.* 6:373-381.

For example, the recombinant RV SPBNGA has been constructed to carry the G gene of strain SAD B19 in which $Arg_{333}$ is replaced with $Glu_{333}$. The $Glu_{333}$ containing G protein, referred to as "GA", renders the virus non-pathogenic. $Arg_{333}$ can be replaced with other amino acids which render it non-pathogenic, for example aspartic acid can be used to replace $Arg_{333}$ to form an $Asp_{333}$ G protein.

The rabies virus may be further attenuated by altering the G gene to provide at least one nucleotide encoding amino acid 194 that resists mutation, as described in U.S. Pat. No. 7,695,724. At least one nucleotide from nucleotides 637-639 encoding the amino acid at position 194 of the glycoprotein is altered by site directed mutagenesis from AAT to for example TCC. This mutation, which replaces asparagine at position 194 in the protein with serine, minimizes the possibility for an Asn→Lys exchange at amino acid position 194 of the G protein. Other degenerate codons for serine may be utilized in a G gene at position 637-639, and other amino acids which minimize the possibility for an Asn→Lys exchange at amino acid position 194 of the GA protein may have their codon inserted at position 637-639 in the G gene. For a GA protein having, for example, the amino acid like serine coded for at amino acid position 194, the mutagenized GA protein may be designated as "GAS" and the recombinant viruses expressing the GAS gene is termed "SPBN-GAS". A recombinant virus comprising two or three GAS genes expressing is termed "SPBNGAS-GAS" and "SPBN-GAS-GAS-GAS", respectively.

The nucleotide sequence of the GAS gene is provided in U.S. Pat. No. 7,695,724 as SEQ ID NO: 5.

In certain embodiments, the recombinant RV may comprise two or more G genes, and in particular two or more G genes containing the attenuating modifications described above. Preparation of recombinant RV comprising multiple G genes is described in U.S. Pat. No. 7,223,584 (SPBNGA-GA), U.S. Pat. No. 7,695,724 (SPBNGAS-GAS), and US Pat. Pub. US-2011-0064764 (SPBNGAS-GAS-GAS).

Attenuation of RV may also be achieved by combining mutations in two different parts of the viral genome, e.g., in the phosphoprotein (P) and the G genes. See US Pat. Pub. 2002-0164356, describing RVs comprising a mutation in the region of the P gene encompassing residues 139-170 and simultaneously replacing $Arg_{333}$ in the G gene.

The attenuated RV is further modified to express a foreign protein antigen. The protein antigen may encode an entire protein, or any immunogenic fragment thereof, which is capable of eliciting an immune response in an immunized host. Thus, by "foreign protein antigen" as used herein is mean to include either a whole protein or any fragment thereof capable of eliciting an immune response in an immunized host. A nucleotide sequence encoding the foreign protein antigen may be inserted in a site that is not necessary for viral infection or replication, where insertion does not significantly interfere with RV infection or replication. Preferred locations of insertion for the foreign protein antigen-expressing gene comprise locations between multiple G gene copies in RV comprising multiple G genes, or between the rabies virus M and L genes.

According to one embodiment, the cDNA plasmid of the vector SPBAANGAS-GAS contains one cloning site that is located between the two GAS genes. This site is used for inserting the cDNA of the protein of choice using standard cloning technology.

Standard recombinant DNA technology can be used to alter an RV genome to achieve attenuation, and to insert genes encoding foreign protein antigens into an RV genome. For example, recombinant RV genomes can be constructed by first obtaining (by cloning, restriction digestion and isolation, or otherwise) one or more modified G protein gene sequences for insertion into an RV genome, to provide for attenuation, and one or more gene sequences encoding one or more foreign protein antigens. Site directed mutagenesis, restriction and re-ligation with heterologous sequences may be employed. Digested with the appropriate restriction enzymes allows the insertion of the additional nucleotide sequences. The proper insertion of the additional nucleotide sequences can be confirmed using techniques such as restriction enzyme analysis and/or DNA sequencing.

Live, infectious viral particles capable of expressing foreign protein antigens upon infection of a recipient cell, for use as vaccines according to the invention, can be recovered or "rescued" by transfecting appropriate host cells with an expression vector containing a recombinant RV genome into which the foreign protein antigen-encoding gene(s) have been inserted. Insertion of the recombinant genome into an expression vector for subsequent transfection into host cells for production of vaccine is within the skill in the art.

The expression vector containing the modified RV genome should comprise a promoter, such as a T7 promoter, which is active in the host cell. For example, BSR cells stably transfected with a T7 polymerase gene, as described in Buchholz et al. (1999), *J. Virol.* 73: 251-259, can be used as a host cell. These cells constitutively express T7 polymerase, which can activate transcription from a T7 promoter contained with the expression vector. At an appropriate time after transfection (e.g., three days), infectious recombinant RV vaccine can be recovered from the culture media of the transfected host cells. Infectivity of the recovered live vaccine can be confirmed by exposing BSR cells to culture media from the transfected host cells, or to the recovered live vaccine. Rescued live vaccine can be visualized in these BSR cells by staining the cell culture with FITC-labeled anti-RV protein antibodies.

The prime/boost regime of the present invention can be used for either pre- or post-exposure immunization, as well as therapeutic immunization against infections by pathogens. The regimen may also be employed as a prophylactic immunization against cancer, or for treatment of cancer.

The subject may comprise a vertebrate, preferably a mammal, most preferably a human being. Subjects for immunization according to the present invention include, for example, humans and other primates, rodents (e.g., mice, rats, and guinea pigs), lagamorphs (e.g., rabbits), bovines (e.g, cattle), ovines (e.g., sheep), caprins (e.g., goats), porcines (e.g., swine), equines (e.g., horses), canines (e.g., dogs), felines (e.g., cats), domestic fowl (e.g., chickens, turkeys, ducks, geese, other gallinaceous birds, etc.).

The foreign protein antigen expressed by the recombinant RV, and provided in the subsequent booster immunization, is an antigen that is target for immune response that will result in treating or preventing disease caused by disease causing agents. The foreign protein antigen may include an antigen of any protein for which immunity is sought or against which antibodies can be raised.

The disease causing agent or disease state has associated with it an antigen which triggers immune recognition and ultimate elimination or control of the disease causing agent or disease state in a host, by initiating a humoral and/or cellular immune response against the associated disease causing agent. Disease causing agents include but are not limited to cancer and pathogenic microorganisms.

Cancers which may be treated using the recombinant rabies virus and boost immunization method of the present invention include but are not limited to primary or metastatic melanoma, brain cancers, thymoma, lymphoma, sarcoma, lung cancer, liver cancer, non-Hodgkins lymphoma, Hodgkins lymphoma, leukemias, uterine cancer, and adenocarcinomas such as breast cancer, prostate cancer, ovarian cancer, pancreatic cancer and the like. A gene encoding an antigen associated with the cancer is incorporated into the recombinant RV virus genome. The antigen associated with the cancer may be expressed on the surface of a cancer cell or may be an internal antigen. Preferred antigens are cell surface molecules.

Cancer-associated antigens which may in whole or in part may comprise the foreign protein antigen expressed by RVs according to the present invention include, for example, Tyrosine kinase 2, Melanoma-associated antigens (MAGE, e.g., MAGE-1 and MAGE-3), MART-1 (melanoma); survivin, AIM-2, MAGE-1, TRP-2, gp100, HER-2 and IL13Rα2 (glioblastoma); prostate-associated antigen (PSA) (prostate cancer), alphafetoprotein (AFP); carcinoembryonic antigen (CEA); CA-125 (ovarian cancer); MUC-1; MCU-2; epithelial tumor antigen (ETA); breast cancer-associated protein 3 (BCA3); c-erb/B2 (breast cancer); breast carcinoma associated MAR-binding Proteins p90 and p70; tyrosinase; abnormal products of ras and abnormal products of p53 (pancreatic cancer); and bladder cancer-associated protein (BLCAP).

In one embodiment the antigen associated with the cancer is a tumor associated antigen (TAA) or portion thereof. Cancer-associated antigens comprising TAAs may be identified, isolated and cloned by methods known in the art such as those disclosed in U.S. Pat. No. 4,514,506.

In another embodiment, the prime/boost immunization combination of the present invention is for a vaccination against a disease causing agent in which the agent is a pathogenic microorganism. The pathogenic microorganisms may comprise a prion, virus, bacterium, protozoan, or yeast. The antigen thus comprises a prion antigen, a viral antigen, a bacterial antigen, a protozoal antigen or a yeast antigen.

Disease causing virus agents include, for example, the following, wherein antigens provided are intended to be exemplary, not limiting: HIV (GP-120, p17, GP-160 antigens); cytomegalovirus; influenza (NP, HA antigen); Hendra virus; herpes simplex (HSVdD antigen); human papilloma virus; equine encephalitis virus; hepatitis virus (Hep B Surface Antigen); neurotropic viruses; Japanese Encephalitis virus; and the like. The virus may also comprise an emerging or re-emerging virus such as Dengue, West Nile Virus, Ebola virus, Nipah virus or Rift Valley Fever virus. The viral antigen may comprise, for example, virus surface proteins or other virus protein antigens.

In one embodiment, the foreign protein antigen is an antigen of the Nipah virus (NiV). NiV is a zoonotic virus belonging to the family Paramyxovirus genus Henipaviruses. The biological properties of NiV, including a broad species tropism, high transmission rate, high mortality in humans, and significant economic impacts on live stock industry have made it a major public and veterinary health concern. Although immune responses necessary for protection against NiV infection have not been completely defined, neutralizing antibodies which are induced by the Nipah virus glycoprotein (NiV-G), are the major effectors against this viral infection. Thus, in one embodiment, the foreign protein antigen is NiV-G or a fragment thereof.

Pathogenic yeast include, for example, *Aspergillus*, invasive *Candida*, and the like.

Protein antigens of prions include proteins such as BSE prion protein and scrapie prion protein.

Pathogenic bacteria include but are not limited to, *Mycobacteria*, Legioniella and the like.

Further known causative agents responsible for diseases from which suitable antigens may be derived include, but are not limited to, *chlamydia*, diphtheria, pertussis, tetanus, tuberculosis, nontuberculous mycobacteria-associated diseases, bacterial and fungal pneumonias, babesiosis, cholera, typhoid, plague, shigellosis, salmonellosis, Legionnaire's Disease, Lyme disease, malaria, hookworm, onchocerciasis, schistosomiasis, trypanosomiasis, leshmaniasis, giardiasis, amoebiasis, filariasis, borreliosis, and trichinosis. The foreign protein antigen for use in the practice of the invention is an antigen associated with the disease, more particularly an antigen of the pathogen causing the disease.

Recombinant RVs expressing a foreign protein antigen can be used to induce an immune response against tumor cells and pathogens which express the protein. Direct delivery of pharmaceutical compositions in vivo will generally be accomplished via injection using a conventional syringe. In this regard, the compositions can be injected either subcutaneously, epidermaly, intradermally, intrathecally, intraorbitally, intramucosally (e.g., nasally, rectally and vaginally), intraperitoneally, intravenously, orally, or intramuscularly. Other modes of administration include oral and pulmonary administration, suppositories, and transdermal applications.

An initial immunization with recombinant RV expressing the foreign protein antigen ("prime immunization") may be followed by additional immunizations of recombinant RV expressing the foreign protein antigen. Depending on the intended mode of administration, the recombinant RV can be included in various pharmaceutical compositions. The compositions may include a pharmaceutically acceptable carrier and, optionally, can include other medicinal agents, pharmaceutical agents, carriers, adjuvants, diluents, and excipients. "Pharmaceutically acceptable" means a material that is not biologically or otherwise undesirable, i.e., the material can be administered to an individual along with the recombinant RV composition without causing any undesirable biological effects or interacting in a deleterious manner with any of the other components of the pharmaceutical composition in which it is contained. Examples of physiologically acceptable carriers include saline solutions such as normal saline, Ringer's solution, PBS (phosphate-buffered saline), and generally mixtures of various salts including potassium and phosphate salts with or without sugar additives such as glucose. Suitable excipients are, for example, water, saline, dextrose, glycerol, and ethanol. Nontoxic auxiliary substances, such as wetting agents, buffers, or emulsifiers may also be added to the composition. In one embodiment, adjuvants are not utilized for immunizations with the recombinant RV expressing foreign protein antigen.

Parenteral administration, if used, is generally characterized by injection. Sterile injectables can be prepared in conventional forms, either as liquid solutions or suspensions, solid forms suitable for solution or suspension in liquid prior to injection, or as emulsions.

According to the invention, an immunologically effective amount of the recombinant RV expressing foreign protein antigen is administered to the subject in need of protection against or treatment of cancer or pathogen-induced disease in order to induce a protective immune response to the foreign protein antigen. An effective immunizing amount given to the subject is one in which a sufficient immunological response to the antigen is attained to provide a medically effective immune response to the cancer or pathogen, when augmented with booster immunizations of adjuvant-free foreign protein antigen. For each recipient, the total vaccine amount to be administered can be deduced from protocols for immunization with other vaccines. The exact amount of recombinant RV expressing the foreign protein antigen will vary from subject to subject, depending on the species, age, weight and general condition of the subject, the particular strain of RV and encoded foreign protein antigen, mode of administration, and the like. The immunologically effective dosage or the effective immunizing amount that inoculates the animal and elicits satisfactory immune response can be easily determined or readily titrated by routine testing such as, for example, by standard dose titration studies. Generally, dosage will approximate that which is typical for the administration of other vaccines. In certain embodiments, a single dose of recombinant RV expressing foreign protein antigen administered to the subject is from about $10^4$ to about $10^6$ tissue culture infectious units (TCIU), more preferably from about $10^5$ to about $10^6$ TCIU. Multiple dosing is also contemplated.

Following the prime immunization, the subject is inoculated at least once with a booster composition containing the foreign protein antigen. The booster composition comprises the foreign protein antigen in a pharmaceutically acceptable carrier. The booster composition may utilize any vehicle suitable for parenteral administration of the foreign protein antigen. The booster composition may contain the carrier substances noted above for formulation of the recombinant RV. However, the booster composition is adjuvant-free. Notwithstanding the absence of adjuvant, the booster immunization results in a significant increase in the production of antibodies specific for the foreign protein.

The booster composition may comprise, in preferred embodiments, phosphate-buffered saline, aqueous sodium chloride, e.g., a 0.9% sodium chloride solution. In one embodiment, the booster composition is dispersed or dissolved in the vehicle providing the booster composition. In one embodiment, the protein antigen is water soluble and is dissolved in an aqueous-based adjuvant-free vehicle, such as saline solution or phosphate-buffered saline. The booster composition may comprise additional ingredients such as stabilizers or other formulation aids, provided that it does not contain adjuvant.

The booster immunization may be administered following initiation of an immune response to the foreign protein antigen by the recombinant RV. Generally, at least about 5 days, more preferably at least about 10 days, should be permitted to lapse following the primary immunization with recombinant RV before boosting. In some embodiments, booster immunization occurs within 1 to 300 days, 5 to 250, 10 to 200, 15 to 150, 20 to 100, or 30 to 60 days following primary immunization with recombinant RV expressing the foreign protein. In specific embodiments, a booster immunization is administered 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 52, 53, 54, 55, 56, 57, 58, 59 or 60 days following primary immunization.

Multiple booster immunizations may be administered to augment the host immune response to the foreign protein antigen. For example, 2, 3, 4, 5, or 6 booster immunizations may be administered in intervals. The intervals between booster immunizations may be uniform, e.g., booster immunizations are spaced apart by 5, 10, 20, 25, or 30 day intervals, or the booster immunizations may be scheduled at irregular time intervals. The progress of the subject's immune response may be monitored by conventional assay methods. For example, the appearance of antibodies to the foreign protein antigen in the blood or serum of the inoculated subject may be monitored by standard antibody assay methods including, but not limited to, radioimmunoassay, ELISA (enzyme-linked immunosorbent assay), "sandwich" immunoassays, immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays. The boost schedule may be revised according to the progress of the individual subject's response.

The treatment regime of the present invention is not limited to a single immunization with recombinant RV. Following the primary immunization with recombinant RV expressing foreign protein antigen, booster immunizations comprising the same or different recombinant RV expressing the foreign protein antigen may be administered. Booster immunizations with foreign protein antigen-expressing RV and free foreign protein may be intercalated to augment and enhance the subject's immune response, as needed.

In one embodiment, a kit is provided comprising two vaccine preparations suitable for parenteral administration. The kit comprises a first composition comprising recombinant RV expressing at least one foreign protein antigen of interest, for immunizing a subject. The kit further comprises a second composition for boosting the immune response of the subject to the foreign protein antigen. The first composition may optionally contain adjuvant. It preferably does not contain adjuvant. The second composition is adjuvant-free. The respective compositions may be in liquid or solid (lyophilized) form.

The kits of the present invention may optionally comprise different containers (e.g., vial, ampoule, test tube, flask or bottle) for each individual composition. The kit may contain additional reagents, such as buffers, diluents and the like, for formulation the individual components. Each component will generally be suitable as aliquoted in its respective container or provided in a concentrated form.

Instructions for using the kit according to the immunization methods described above may be included. The instructional material may comprise a publication, a recording, a diagram, or any other medium of expression which can be used to communicate the usefulness of the method of the invention in the kit for assessment of oocyte quality. A package insert may comprise text housed in any physical medium, e.g., paper, cardboard, film, or may be housed in an electronic medium such as a diskette, chip, memory stick or other electronic storage form. The instructional material of the kit of the invention may, for example, be affixed to a container which contains other contents of the kit, or be shipped together with a container which contains the kit. Alternatively, the instructional material may be shipped separately from the container with the intention that the instructional material and the contents of the kit be used cooperatively by the recipient.

In certain embodiments of the invention, the prime/boost regimen constitutes immunization against NiV, and the foreign protein expressed by the recombinant RV and provided in soluble form in the boost composition comprises NiV-G, or an immunogenic fragment thereof. As described in the Examples below, immunization with the recombinant RV SPBAANGAS-NG-GAS, the highly attenuated live rabies recombinant vaccine expressing NiV-G, produced antibodies that recognized NiV-G and are able to neutralize NiV. Antibody titers were however, low. Booster immunization with the same preparation resulted in a strong anamnestic antibody response and the amount of virus-neutralizing antibody, which correlated with NiV-G-binding antibody titers, depended on the vaccine concentration used for the primary immunization. Mice which received primary and secondary immunization with the recombinant RV SPBNGAS-GAS did not develop any NIV-neutralizing or NIV-G-binding antibodies, but mice primed with SPBNGAS-GAS and then boosted with SPBAANGAS-NG-GAS showed an anamnestic NiV-G-specific antibody response.

Moreover, the development of the anamnestic anti-NiV-G response was not solely mediated by the RV vector. Mice were first immunized with SPBAANGAS-NG-GAS or SPBNGAS-GAS and boosted with soluble adjuvant-free NiV-G. Only the mice that were primed with SPBAANGAS-NG-GAS developed a strong anamnestic anti-NIV-G antibody response, indicating that immunization with SPBAANGAS-NG-GAS induces immunological memory that is largely NiV-G-specific.

A requirement for any vaccine is its ability to induce long-lasting immunity. Mice immunized twice with SPBAANGAS-NG-GAS displayed anti NiV-G Ig titers determined at 176 days after the second immunization, similar to those determined 10 days after the second immunization. Anti-NiV antibody titers strongly increased after a third immunization with soluble adjuvant-free NiV-G at 195 days after the second immunization with SPBAANGAS-NG-GAS.

The immune response achieved by prime immunization with a recombinant RV expressing a foreign protein antigen, followed by booster immunization with the corresponding soluble foreign protein antigen in an adjuvant-free preparation, is more robust than an immune response achieved by prime and boost immunizations with the soluble foreign protein alone. When mice receiving prime and booster inoculations with soluble NiV-G three weeks apart, no significant amounts of NiV-G-specific antibodies were produced after the primary immunization. The booster immunization with NiV-G resulted in the production of only low anti-NG antibody titers. Moreover, only IgG 1 and no IgG 2 isotypes were produced after the prime/boost immunization with soluble NiV-G alone.

Immunization with two consecutive doses of SPBAANGAS-NG-GAS induced a strong long-lasting anti-NiV-G response. The response, however, drastically increased after an additional immunization with adjuvant-free soluble NiV- G. Primary immunization with SPBAANGAS-NG-GAS followed by a booster immunization with adjuvant-free soluble NiV-G soluble NG also induced also high titers of NG-specific antibodies. The adjuvant-free soluble NiV-G booster immunization that was administered after the primary and secondary immunizations with SPBAANGAS-NG-GAS induced predominantly IgG 2A and IgG 2B isotypes, suggesting that SPBAANGAS-NG-GAS stimulates a Th1-dominant response against NiV-G.

The practice of the invention is illustrated by the following non-limiting example. The invention should not be construed to be limited solely to the compositions and methods described herein, but should be construed to include other compositions and methods as well. One of skill in the art will know that other compositions and methods are available to perform the procedures described herein.

EXAMPLES

Preparative Example 1

Recombinant Rabies Virus Vectors SPBNGAS and SPBNGAS-GAS

Production of the recombinant RV vectors SPBNGAS and SPBNGAS-GAS is described in U.S. Pat. No. 7,695,724. Recombinant RV vaccine SPBNGAS is based on the prototype recombinant virus SPBN, which was derived from the SAD B19 cDNA clone (Schnell et al., 1994, *EMBO J* 13:4195-4203).

To reduce the pathogenicity of the RV vaccine vector SPBN, the SPBN G gene was replaced with a similar G gene encoding a single amino acid exchange, $Arg_{3333} \rightarrow Glu_{333}$ to form the vector SPBN-GA. The mutant G gene encoding the $Arg_{3333} \rightarrow Glu_{333}$ substitution is designated as "GA". For this approach, the RV G gene was amplified by PCR using Vent polymerase (New England Biolabs, Beverly, Mass.) from SN10-333 (Morimoto et al., Vaccine 19:3543-3551, 2001) and cloned into SPBN. The resulting plasmid was designated pSPBN-GA. To construct a recombinant RV expressing two identical RV Gs, the G gene was amplified by PCR using Ventpolymerase, with SN10-333 as a template, and primers SN-10 BsiWI (sense; CGATGTATACGTAC-GAAGATGTTCCTCAGCTCTCCTG [BsiWI site underlined, start codon in boldface] (SEQ ID NO:1)), and SN-10 NheI (antisense; CTTATCAGCTAGCTAGCTAGTTACA-GTCTGTCTCACCCCCA [NheI site underlined, stop codon in boldface] (SEQ ID NO:2). The PCR product was digested with BsiWI and NheI (New England Biolabs) and ligated to pSPBNGA, which had been digested previously with BsiWI and NheI. The resulting plasmid was designated pSPBN-GAGA.

To stabilize the nonpathogenic phenotype and prevent reversion of SPBN-GA to the pathogenic phenotype through an $Asn_{194} \rightarrow Lys_{194}$ mutation in GA, $Asn_{194}$ was exchanged with $Ser_{194}$; reversion to the pathogenic phenotype would require three base exchanges instead of one. The thus further mutagenized GA gene (ATT TCC) is designated "GAS". The GAS gene was reintroduced into the RV vector SPBNGA, resulting in the vector SPBNGA-S. The vector pSPBNGAS-GAS, containing two copies of the GAS gene, was obtained by inserting an extra copy of the glycoprotein gene from pSPBNGA-S as described above for the construction of pSPBNGAGA.

The correct nucleotide sequences of the inserted genes were confirmed by reverse transcription-PCR and DNA sequencing as follows. For nucleotide sequence analysis, BSR cells grown inT25 tissue culture flasks were infected with the rescued viruses and incubated for 3 days at 34° C. Then the cells were washed with phosphate-buffered saline (PBS), and RNA was extracted using the RNeasy mini-kit (QIAGEN, Valencia, Calif.) according to the manufacturer's protocol. For synthesis of RV G cDNA from genomic RV RNA, Superscript One-Step RT-PCR (Invitrogen, Carlsbad, Calif.) and primers SADB19 −120seq(+) (AACATGT-TATGGTGCCAT TAAACCGCT) (SEQ ID NO:3) and SADB19 +50seq(−) (GGG TGT TAG TTT TTT TCA TGG ACT TGG) (SEQ ID NO:4) were used. To synthesize RV G cDNA from the second G gene of SPBNGA-GA, primers SBsi2seq(+) (TAA TTA ACG TCC TTT CAA CGA TCC) (SEQ ID NO:5) and SNhe2seq(−) (GAG CAT CTT GAA GTA AGT AGT CTC AGG T) (SEQ ID NO:6) were used. PCR-amplified products were subjected to nucleotide sequencing and the complete nucleotide sequences of the G gene(s) were obtained and analyzed for presence of mutations.

Preparative Example 2

Recombinant Rabies Virus Vector SPBAANGAS-GAS

To facilitate insertion of foreign antigen genes into the SPBNGAS vector, AsiSI and AscI restriction sites were introduced. A fragment of pSPBNGAS containing intergenic and regulatory sequences between PacI and BsiWI was amplified using Deep Vent polymerase (New England Biolabs, Inc., Beverly, Mass.) and primers InterG BA(+) (5'-CGA TGT ATA CGTACG TTT TTG CGA TCG CCG TCC TTT CAA CGA TCC AAG TC-3'[BsiWI site underlined; AsiSI site in boldface] (SEQ ID NO:7)) and InterG AN(−) (5'-CTT AGC GCTAGC AAA AAG GCG CGC CGG AGG GGT GTT AGT ITT TTT CAT G-3'[NheI site underlined; AscI site in boldface] (SEQ ID NO:8)). The PCR product was digested with BsiWI and NheI and ligated into RV vaccine vector pSPBNGAS, previously digested with BsiWI and NheI resulting in the vector designated as pSPBAAN-GAS. A second copy of GAS gene was inserted into pSPBAANGAS between AscI and NheI in the similar manner using primers that contain the AscI and NheI sites:

```
SADB19 AscI(+)
                                      (SEQ ID NO: 9))
(5'-CGA ATT TAT TGG CGC GCC AAG ATG GTT CCT

CAG GCT CTC CTG-3' [AscI site underlined;
start codon in boldface
and

SADB19 NheI(-)
                                      (SEQ ID NO: 10))
(5'-CTT ATC AGC TAG CTA GCT AGT TAC AGT CTG

GTC TCA CCC CCA-3' [NheI site underlined;
stop codon in boldface]
``` resulting in pSPBAANGAS-GAS. The presence of the introduced fragments was confirmed by restriction analysis and sequencing.

Preparative Example 3

Recombinant Rabies Virus Vector SPBAANGAS-NG-GAS

The NiV G gene was cloned into or pSPBAANGAS-GAS as follows, resulting in the double GAS variant pSPBAAN- GAS-NG-GAS. The NiV G gene was amplified using Deep Vent polymerase (New England Biolabs, Inc., Beverly, Mass.) and the G gene-specific primers

```
NGB(+)
                                    (SEQ ID NO: 11))
(5'-CCG GAA TTC CGT ACG AAG ATG CCG GCA

GAA AAC AAG AAA GTT AGA TTC GA -3'
[BsiWI site underlined; start codon
in boldface]
and
NGA2(-)
                                    (SEQ ID NO: 12))
(5'- TGC TCT AGA GCG ATC GCC GTT TAT GTA CAT TGC TCT GGT ATC TTA ACC -3'
[AsiSI site underlined; stop codon
in boldface].
```

BsiWI and AsiSI recognition sites were introduced at the 5' and 3' of the NiV G gene (underlined). The PCR product was digested with BsiWI and AsiSI and ligated into RV vaccine vector pSPBAANGAS-GAS, previously digested with BsiWI and AsiSI. The presence of inserts and the flanking sequences were confirmed by sequencing.

Preparative Example 4

Recombinant Rabies Virus Vector SPBAANGAS-OV-GAS

The OV gene was cloned into pSPBAANGAS-GAS following similar methodology as described for pSPBAAN-GAS-NG-GAS, resulting in the double GAS variant pSPBAANGAS-OV-GAS. Briefly, OVA cDNA was synthesized (GenScript), amplified in *Escherichia coli*, and then cloned into pSPBAANGAS-GAS resulting in pSPBAANGAS-OVA-GAS. The presence of the OVA insert and the flanking sequences was confirmed by sequencing.

Preparative Example 5

Rescue of SPBNGAS, SPBNGAS-GAS, SPBNGAS-OVA-GAS and SPBNGAS-NG-GAS from cDNA clones and Assessment of NG and OVA Expression To rescue the recombinant viruses, BSR cells were transfected with a calcium phosphate transfection kit (Stratagene, La Jolla, Calif.) with 5.0 µg of pSPBNGAS, pSPBNGAS-GA, pSPBAANGAS-NG-GAS or pSPBAANGAS-OVA-GAS and 5.0 µg of pTIT-N, 2.5 µg of pTIT-P, 2.5 µg of pTIT-L, and 2.0 µg of pTIT-G. After a 3-day incubation, supernatants were transferred onto BSR cells, and incubation continued for 3 days at 37° C. Cells were examined for the presence of rescued virus by immunostaining with fluorescein isothiocyanate (FITC)-labeled anti-RV N protein antibody (Centocor, Malvern, Pa.).

To analyze the expression of NG, BSR cells were infected with SPBAANGAS-NG-GAS. To detect expression of NG, cells were incubated for 24 h, then fixed with 4% paraformaldehyde, incubated with NiV G-specific mouse monoclonal antibody, followed by FITC-conjugated anti-rabbit antibody, and surface expression of NG was determined by flow cytometry. To analyze the expression of OVA, BSR cells were infected with SPBAANGAS-OVA-GAS, incubated for 48 h, and then lysed with lysis buffer. The presence of OVA in the lysate was detected by Western blot analysis using a rabbit anti OVA antibody.

Example 6

Prime/Boost Immunization with SPBAANGAS-OVA-GAS and Soluble OVA

Mice were immunized intra-muscularly (i.m.) with SPBAANGAS-OVA-GAS or a similar vector lacking the gene encoding ovalbumin (SPBAAGAS-GAS), followed by an i.m. booster immunization with SPBAANGAS-OVA-GAS and third immunization with soluble adjuvant-free ovalbumin (OVA), as follows.

Eight to 10 week-old female Swiss Webster mice were first immunized intramuscularly 100 µl phosphate-buffered saline (PBS) containing with $10^5$ FFU of SPBAAGAS-OVA-GAS or SPBAAGAS-GAS. Twenty eight days later, all mice received a booster immunization with 100 µl PBS containing $10^5$ FFU of SPBAAGAS-OVA-GAS. Twenty five days after the booster immunization the mice were hyperimmunized i.m. with 100 µl PBS containing 100 µg of soluble ovalbumin. The mice were bled at 24 days after the primary immunization, 11 days after the booster immunization, and 10 days after the third immunization. Serum samples were collected after each immunization and analyzed for the presence of anti-ovalbumin antibodies.

Ovalbumin antibody titers were measured by ELISA for total immunoglobulin (Whole IgG), IgG1 and IgG2A (FIG. 1). In each box in FIG. 1, the left-hand bar represents mice initially immunized with SPBAAGAS-GAS, while the right-hand bar represents mice initially immunized with SPBAAGAS-OVA-GAS. The primary vaccination with each vector (FIG. 1, column A) induced a weak ovalbumin antibody response which increased only slightly after booster immunization (FIG. 1, column B). Hyper-immunization by the administration of soluble ovalbumin resulted in a significant increase in the production of anti-ovalbumin antibodies (FIG. 1, column C). Notably, mainly IgG 2A antibodies and no significant amounts of IgG 1 antibodies against OVA were produced after the different immunizations, which indicates a predominant TH 1 response.

Comparative Example 7

Prime/Boost Immunization with SPBAANGAS-NG-GAS

Mice were immunized intra-muscularly (i.m.) with SPBAANGAS-NG-GAS, followed by an i.m. booster immunization with SPBAANGAS-NG-GAS, as follows.

Figure 2:
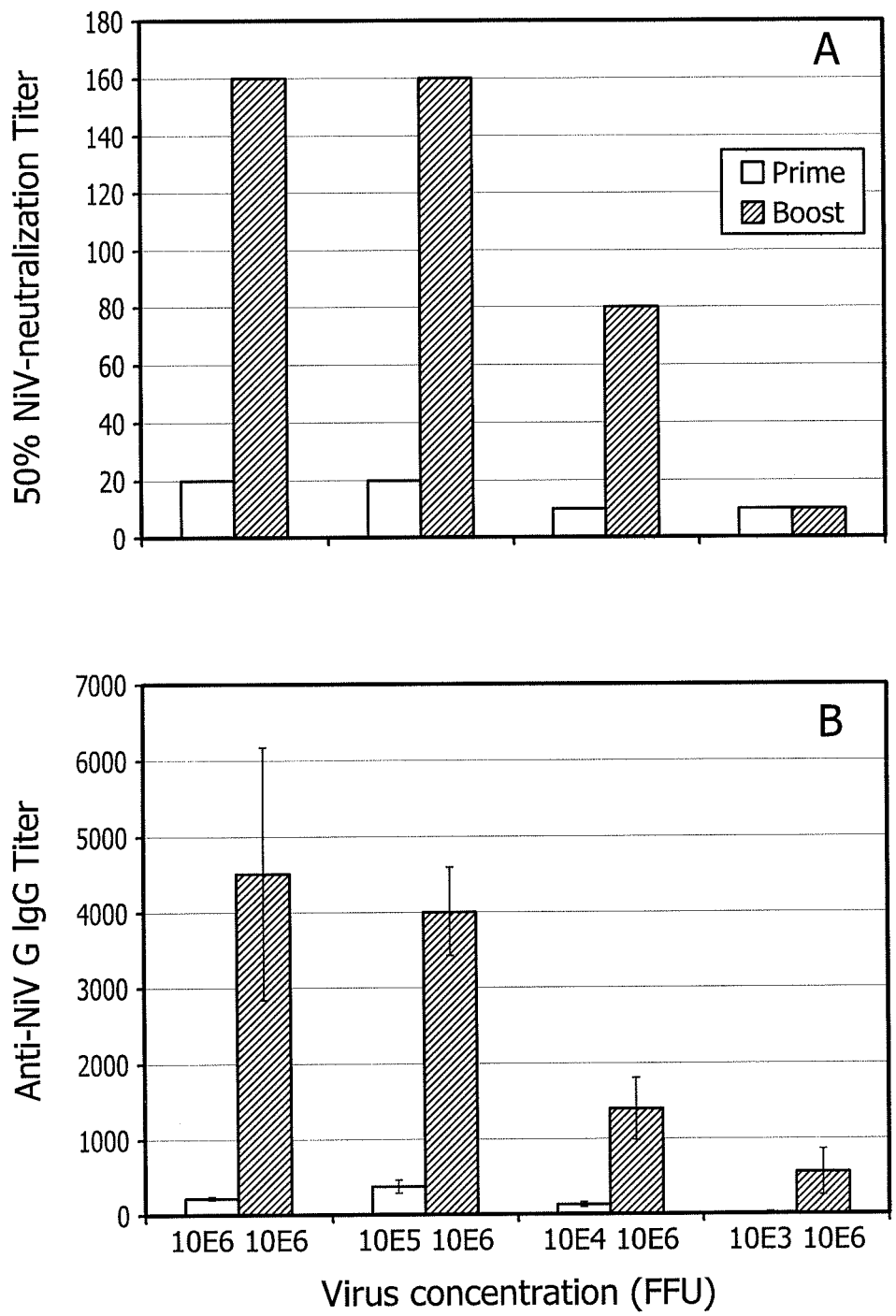
FIG. 2 shows graphs f the production of Nipah virus (NiV) neutralizing antibodies (panel A) and NiV glycoprotein (NiV-G)-binding antibodies (panel B). Mice were immunized with different concentrations ($10^3$-$10^6$ FFU) of the RV variant SPBAANGAS-NG-GAS, then bled at 21 days after the primary immunization and 10 days after the booster immunization. NiV neutralization titers were determined using pooled serum. The results are shown in FIG. 2, panel A (NiV neutralizing antibodies) and panel B (NiV-G binding antibodies). In each pair of bars, the left-hand bar represents antibody titer after prime immunization; the right-hand bar represents antibody titer after booster immunization. NiV-G-binding titers are presented as mean values±standard error.

Groups of ten 6-8 week-old female Swiss Webster mice were immunized i.m. with 100 µl PBS containing different concentrations ($10^3$ to $10^6$ FFU) of SPBAANGAS-NG-GAS and 29 days later received an i.m. booster immunization with 100 µl PBS containing $10^6$ FFU of SPBAANGAS-NG-GAS. The mice were bled at 21 days after the primary immunization and 10 days after the booster immunization. NiV neutralizing antibodies and NiV-G binding antibodies were measured using an ELISA or a micro neutralization test, respectively. NiV neutralization titers were determined using pooled serum. The results are shown in FIG. 2 (panel A: NiV neutralizing antibodies; panel B: NiV-G binding antibodies). In each pair of bars, the left-hand bar represents antibody titer after prime immunization; the right-hand bar represents antibody titer after booster immunization. NiV-G-binding titers are presented as mean values±standard error.

The results of the primary immunization demonstrate that the immunized mice produced antibodies that recognized NiV-G and were able to neutralize NiV, although the antibody titers were low. The primary immunization with SPBAANGAS-NG-GAS also triggered immunological memory against NiV-G, since the booster immunization with $10^5$ FFU of the same vaccine resulted in a strong anamnestic antibody response. The amount of virus-neutralizing antibody, which correlated with the NiV-G-binding antibody titers, depended on the vaccine concentration used for the primary immunization.

Comparative Example 8

Figure 3:
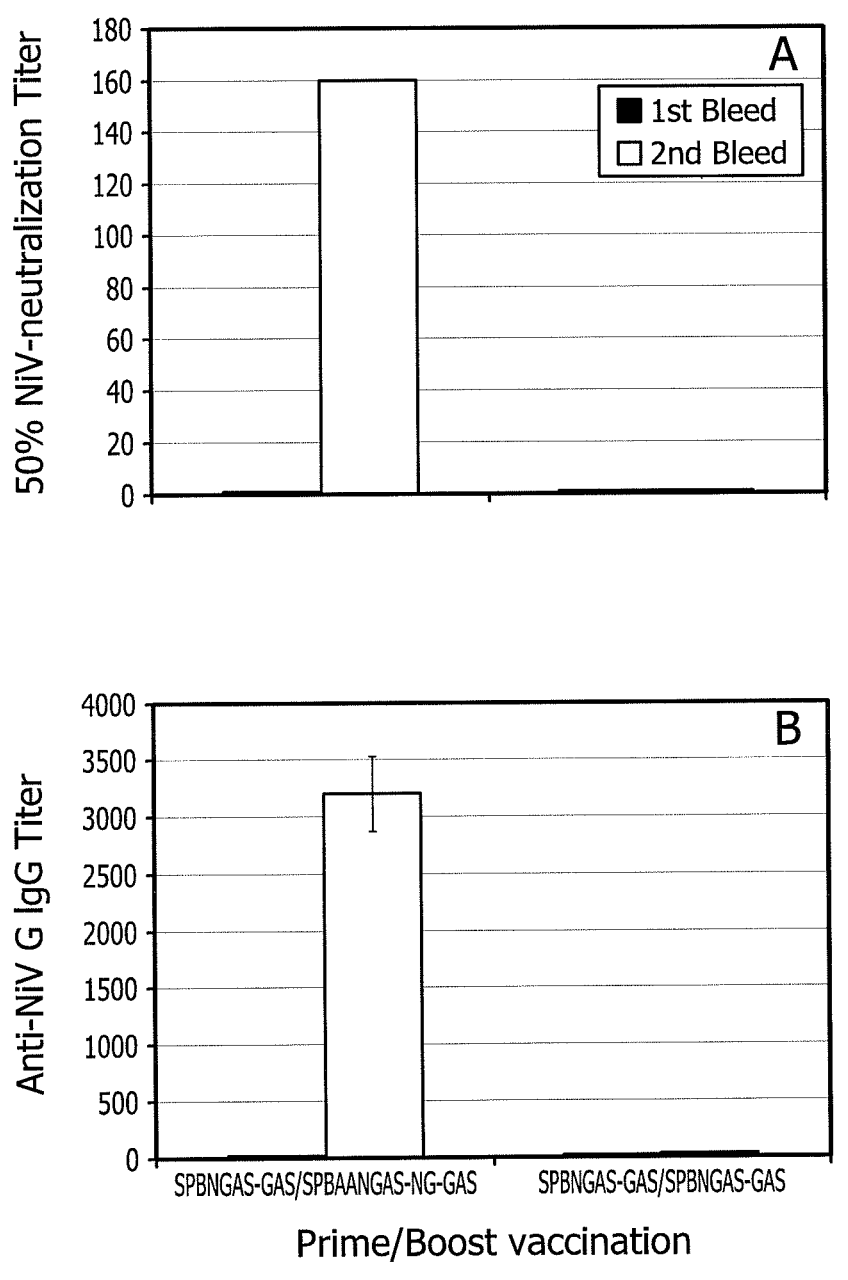

Prime Immunization with SPBAANGAS, Followed by Booster Immunization with SPBAANGAS-NG-GAS Two groups of 10 6-8 week-old female Swiss Webster mice were first immunized i.m. with 100 µl PBS containing $10^5$ FFU of the RV variant SPBNGAS-GAS. At 29 days after the primary immunization one group of mice received a booster immunization with 100 µl PBS containing $10^5$ FFU SPBAANGAS-NG-GAS while the other group was immunized again with 100 µl PBS containing $10^5$ FFU SPBN-GAS-GAS. The mice were bled at 21 days after the primary immunization and 10 days after the booster immunization and NiV neutralizing antibodies and NiV-G binding antibodies were measured using an ELISA or a micro neutralization test, respectively. NiV neutralization titers were determined using pooled serum. The results are shown in FIG. 3: Panel A, NiV neutralizing antibodies; panel B, NiV-G binding antibodies. NiV-G-binding titers are presented as mean values±standard error.

The results show that while mice which received primary and secondary immunization with $10^5$ FFU SPBNGAS-GAS (bars marked SPBNGAS-GAS/SPBNGAS-GAS in FIG. 3) did not develop any NIV-neutralizing or NIV-G-binding antibodies, mice primed with $10^5$ FFU SPBNGAS-GAS and then boosted with $10^5$ FFU SPBAANGAS-NG-GAS (bars marked SPBNGAS-GAS/SPAANGAS-NG-GAS in FIG. 3) showed an anamnestic NiV-G-specific antibody response.

Example 9

Figure 4:
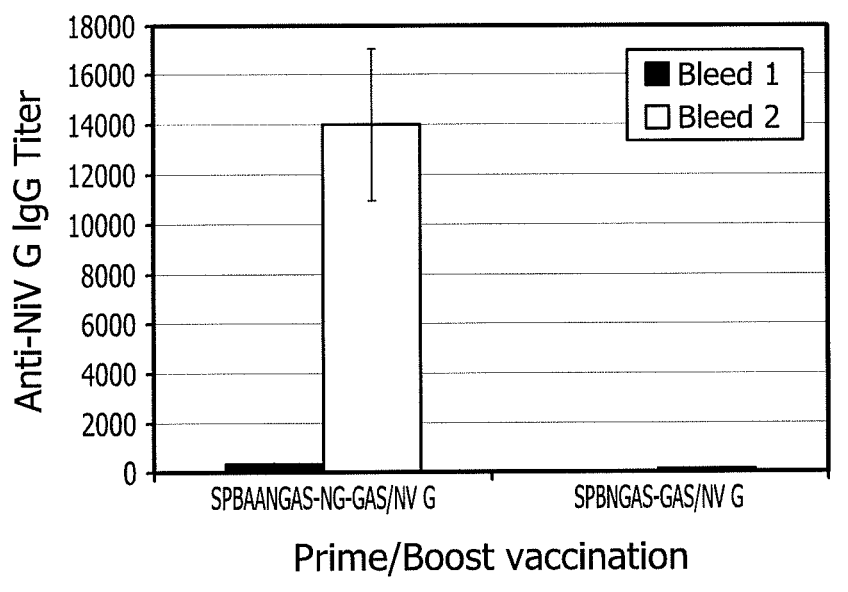

Prime Immunization with SPBAANGAS-NG-GAS, Followed by Booster Immunization with Soluble Nipah Virus Glycoprotein Two groups of 10 6-8 week-old female Swiss Webster mice were first immunized i.m. with 100 µl PBS containing $10^5$ FFU SPBAANGAS-NG-GAS or $10^5$ FFU of the RV variant SPBNGAS-GAS. Twenty-three days later, both groups of mice received an i.m. booster immunization with 100 µl PBS containing 12 µg recombinant-expressed soluble adjuvant-free Nipah Virus Glycoprotein (NiV-G). The mice were bled at 19 days after the primary immunization (left-hand bars in each bar pair in FIG. 4) and 10 days after the booster immunization (right-hand bars in each bar pair). NiV-G-binding antibodies were measured using an ELISA. NiV-G-binding titers are presented as mean values±standard error in FIG. 4. Only the mice that were primed with SPBAANGAS-NG-GAS (SPBAANGAS-NG-GAS/NG in FIG. 4) developed a strong anamnestic anti-NiV-G antibody response, indicating that immunization with SPBAANGAS-NG-GAS induces immunological memory that is largely NiV-G-specific.

Example 10

Prime Immunization with SPBAANGAS-NG-GAS, Followed by Booster Immunization with Soluble Nipah Virus Glycoprotein—Duration of Effect A group of ten 6-8 week-old female Swiss Webster mice was immunized i.m. twice, on day zero and day 29 with 100 µl PBS containing $10^5$ FFU SPBAANGAS-NG-GAS. One hundred ninety-five days after the second immunization, the mice received an i.m. booster immunization with 100 µL PBS containing 12 µg recombinant-expressed soluble NiV-G. The mice were bled at 21 days after the primary immunization (Bleed 1), 10 and 176 days after the second immunization (Bleed 2 and Bleed 3), and 10 days after the third immunization (Bleed 4). See timeline A in FIG. 5. NiV-neutralizing antibodies (panel B in FIG. 5), whole anti-NiV-G-specific antibodies (panel C), and NG-specific IgM, IgG 1, IgG 2A, and IgG 2B isotypes (panel D) were measured using an ELISA. NiV neutralization titers were determined using pooled serum. NiV-G-binding titers are presented as mean values±standard error.

Figure 5:
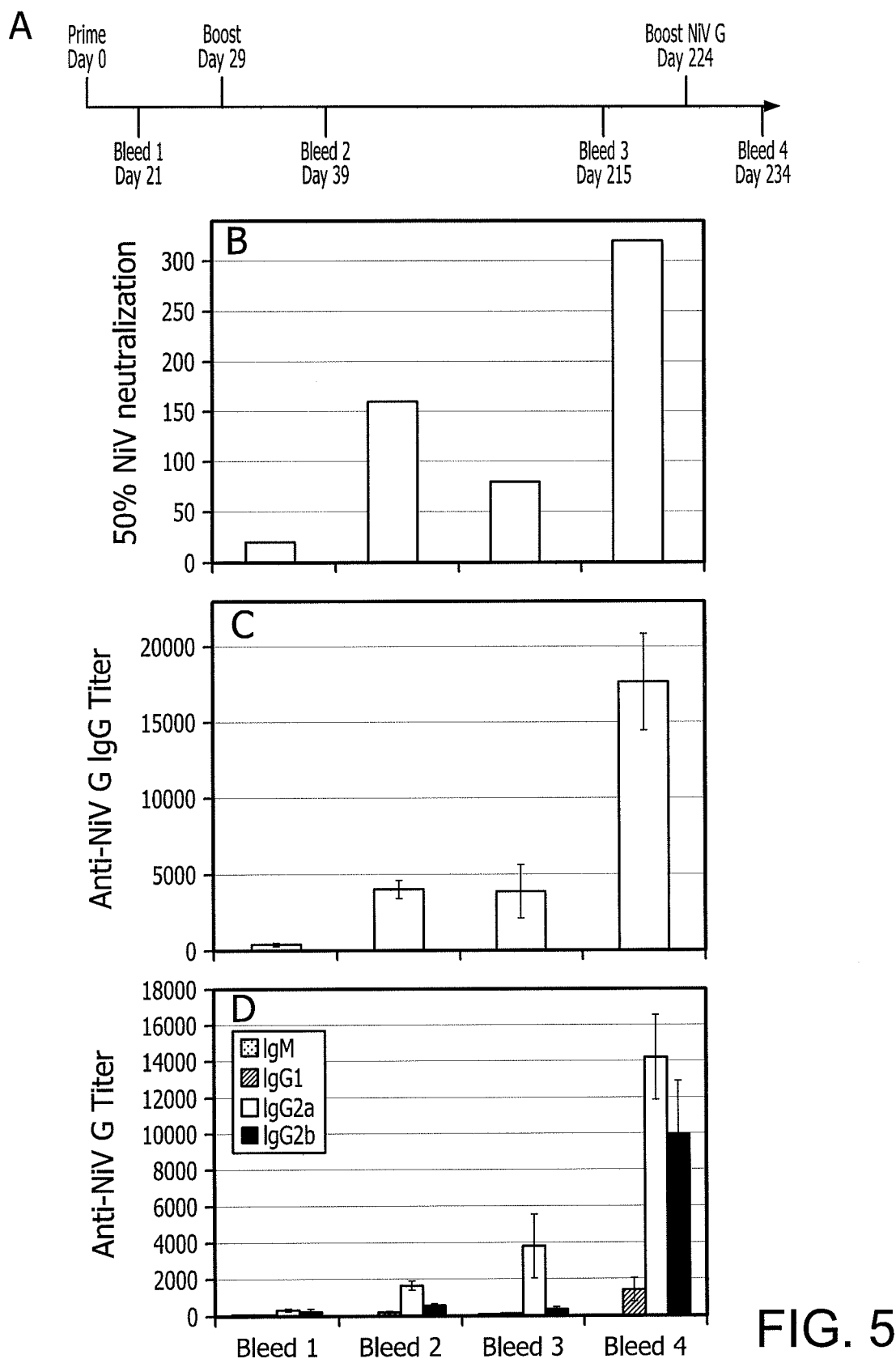

As shown in FIG. 5, the anti NiV-G Ig titers determined at 176 days (Bleed 3) after the second immunization were similar to those determined 10 days (Bleed 2) after the second immunization. Furthermore, anti-NiV antibody titers strongly increased (Bleed 4) after a third immunization with soluble NiV-G at 195 days after the second immunization with SPBAANGAS-NG-GAS.

Comparative Example 11

Figures 6A, 6B:
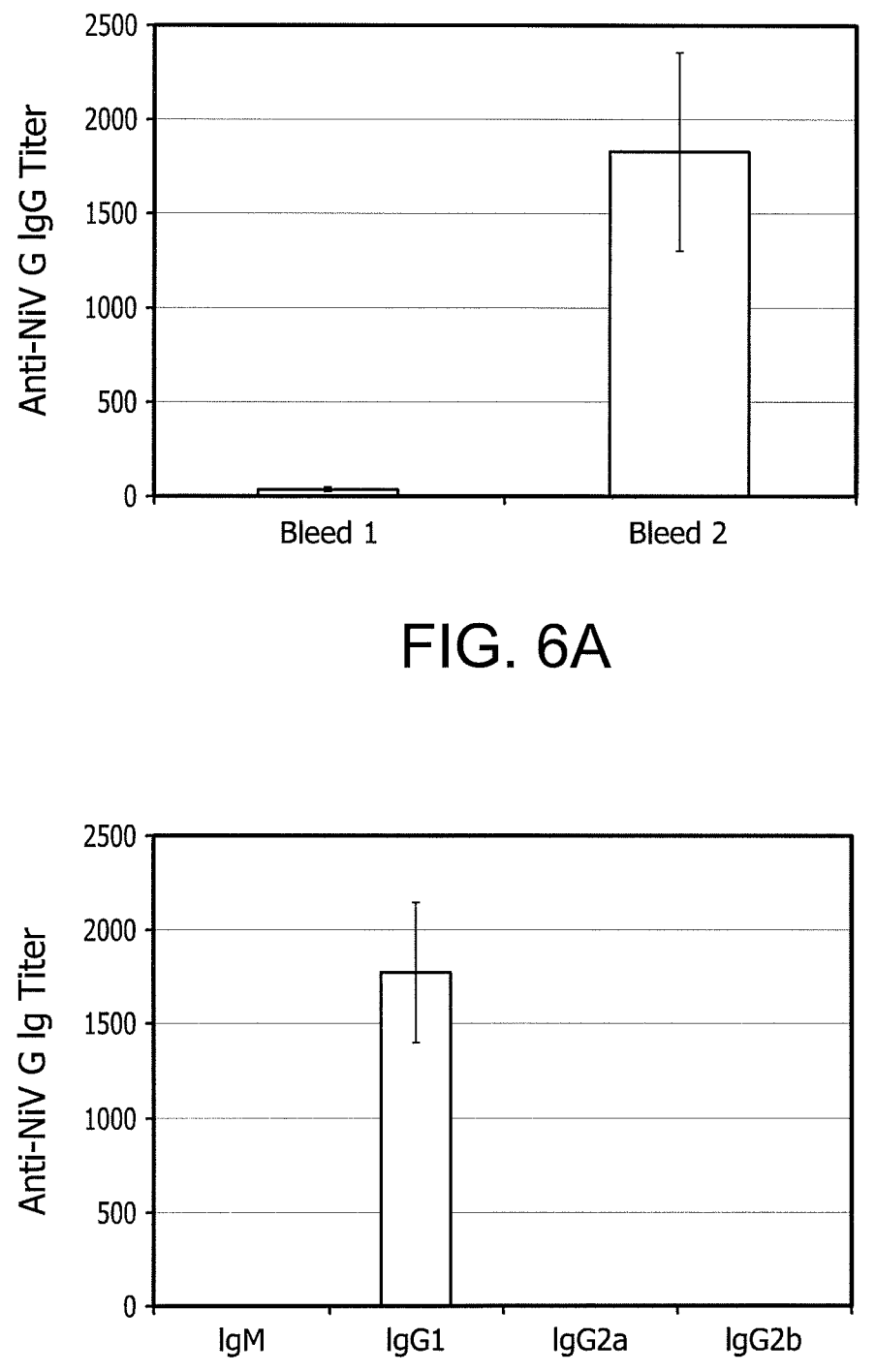

Prime Immunization and Booster Immunization with Soluble Nipah Virus Glycoprotein Groups of ten 6-8 week-old female Swiss Webster mice were immunized i.m. with 100 µl PBS containing 12 µg of NiV-G and 3 weeks later received an i.m. booster immunization with 100 µl PBS containing 12 µg NiV-G. The mice were bled at 10 days after the primary immunization and 10 days after the booster immunization. Total NiV-G binding antibodies were measured using an ELISA. Results are shown in FIG. 6A for the two bleeds. Laso, NiV-G-specific IgM, IgG 1, IgG 2A, and IgG 2B isotypes produced after booster immunization were measured using an ELISA. The results are shown in FIG. 6B. NiV-G-binding titers are presented as mean values±standard error.

Whereas no significant amounts of NiV-G-specific antibodies were produced after the primary immunization, the booster immunization with NiV-G resulted in the production of relatively low anti-NiV-G antibody titers (FIG. 6A). Notably, only IgG 1 and no IgG 2 isotypes were produced after the prime/boost immunization with NiV-G alone, indicating a TH2 response (FIG. 6B).

The disclosures of each and every patent, patent application, and publication cited herein are hereby incorporated herein by reference in their entirety.

One skilled in the art will readily appreciate that the present invention is well adapted to carry out the objects and obtain the ends and advantages mentioned, as well as those inherent therein. While the invention has been disclosed with reference to specific embodiments, it is apparent that other embodiments and variations of this invention may be devised by others skilled in the art without departing from the true spirit and scope used in the practice of the invention. The appended claims are intended to be construed to include all such embodiments and equivalent variations.

The invention claimed is:

1. A method of eliciting an immune response in a subject, comprising the steps of:

(a) providing an attenuated recombinant rabies virus encoding for at least one foreign protein antigen operably linked to control sequences, wherein the foreign protein antigen is located between two G genes in the genome of said attenuated recombinant rabies virus and is not expressed in the structure of the recombinant virus; wherein said control sequences direct the expression of said foreign antigen in a suitable recipient cell infected by said virus; wherein the attenuated recombinant rabies virus contains a mutation wherein the amino acid 333 is glutamic acid and wherein the amino acid 194 is serine in the glycoprotein;

(b) infecting a recipient cell with said rabies virus into a recipient cell of said subject under conditions that permit the expression of said one or more foreign protein antigens by the recipient cell, thereby eliciting an immune response to said foreign protein antigen;

(c) boosting said immune response to said foreign protein antigen by administering to said subject said foreign protein antigen contained in a booster composition which is adjuvant-free; and (d) generating a T cell and B cell response in said subject.

2. The method according to claim 1 wherein the foreign protein antigen comprises a prion protein antigen.

3. The method of claim 1, wherein said foreign protein antigen comprises at least one antigen selected from the group consisting of cancer-associated antigens, viral antigens, bacterial antigens, and protozoal antigens.

4. The method according to claim 3, wherein the cancer-associated antigen is selected from the group consisting of AIM-2, alphafetoprotein, bladder cancer-associated protein, breast carcinoma associated MAR-binding proteins p90 and p70, breast cancer-associated protein 3, carcinoembryonic antigen, CA-125, epithelial tumor antigen, c-erb/B2, gp100, HER-2, IL13Rα2, MAGE-1, MART-1, melanoma-associated antigens, MUC-1, MCU-2, prostate-associated antigen, abnormal products of p53, abnormal products of ras, survivin, tyrosinase, TRP-2 and tyrosine kinase 2.

5. The method according to claim 3 wherein the foreign protein antigen is a viral antigen.

6. The method according to claim 5 where the viral antigen is an antigen of a virus selected from the group consisting of cytomegalovirus, Dengue, Ebola virus, equine encephalitis virus, hepatitis virus, HIV, Hendra virus, herpes simplex virus, human papilloma virus, influenza, Japanese Encephalitis virus, neurotropic viruses, Nipah virus, Rift Valley Fever virus and West Nile Virus.

7. The method according to claim 6, wherein the viral antigen is an antigen of Nipah virus G gene.

8. The method according to claim 3 wherein the foreign protein antigen is an antigen of a pathogen which is associated with chlamydia, diphtheria, pertussis, tetanus, tuberculosis, nontuberculous mycobacteria-associated disease, bacterial and fungal pneumonias, babesiosis, cholera, typhoid, plague, shigellosis, salmonellosis, Legionnaire's Disease, Lyme disease, malaria, hookworm, onchocerciasis, schistosomiasis, trypanosomiasis, leshmaniasis, giardiasis, amoebiasis, filariasis, borreliosis, or trichinosis.

9. The method according to claim 1 wherein the attenuated recombinant rabies virus comprises two or more G genes.

10. The method according to claim 9 wherein a nucleotide sequence encoding the at least one foreign protein antigen is located between two G genes in the genome of said attenuated recombinant rabies virus.

11. The method according to claim 1 wherein a nucleotide sequence encoding the at least one foreign protein antigen is located between the M and L genes in the genome of said attenuated recombinant rabies virus.

12. The method according to claim 1, wherein the attenuated recombinant rabies virus encoding at least one foreign protein is introduced into a recipient cell of the subject without adjuvant.

13. The method according to claim 1, wherein the adjuvant-free booster composition comprises saline or phosphate-buffered saline.

14. A kit for immunization of a subject comprising:

(a) a first composition comprising an attenuated recombinant rabies virus encoding for at least one foreign protein antigen operably linked to control sequences, wherein the foreign protein antigen is located between two G genes in the genome of said attenuated recombinant rabies virus and is not expressed in the structure of the recombinant virus; wherein said control sequences direct the expression of said foreign antigen in a suitable recipient cell infected by said virus; wherein the attenuated recombinant rabies virus contains a mutation wherein the amino acid 333 is glutamic acid and wherein the amino acid 194 is serine in the glycoprotein;

(b) a second composition comprising the at least one foreign protein antigen, wherein said second composition is adjuvant-free.

15. A kit according to claim 14, wherein said first composition is adjuvant-free.

16. The kit according to claim 14, wherein the at least one foreign protein antigen comprises a prion protein antigen, a cancer-associated antigen, a viral antigen, a bacterial antigen, or a protozoal antigens.

17. The kit according to claim 16, wherein the cancer-associated antigen is selected from the group consisting of AIM-2, alphafetoprotein, bladder cancer-associated protein, breast carcinoma associated MAR-binding proteins p90 and p70, breast cancer-associated protein 3, carcinoembryonic antigen, CA-125, epithelial tumor antigen, c-erb/B2, gp100, HER-2, IL13Rα2, MAGE-1, MART-1, melanoma-associated antigens, MUC-1, MCU-2, prostate-associated antigen, abnormal products of p53, abnormal products of ras, survivin, tyrosinase, TRP-2 and tyrosine kinase 2.

18. The kit according to claim 16 wherein the viral antigen is an antigen of a virus selected from the group consisting of cytomegalovirus, Dengue, Ebola virus, equine encephalitis virus, hepatitis virus, HIV, Hendra virus, herpes simplex virus, human papilloma virus, influenza, Japanese Encephalitis virus, neurotropic viruses, Nipah virus, Rift Valley Fever virus and West Nile Virus.

19. The kit according to claim 16 wherein the foreign protein antigen is an antigen of a pathogen which is associated with chlamydia, diphtheria, pertussis, tetanus, tuberculosis, nontuberculous mycobacteria-associated disease, bacterial and fungal pneumonias, babesiosis, cholera, typhoid, plague, shigellosis, salmonellosis, Legionnaire's Disease, Lyme disease, malaria, hookworm, onchocerciasis, schistosomiasis, trypanosomiasis, leshmaniasis, giardiasis, amoebiasis, filariasis, borreliosis, or trichinosis.

20. The kit according to claim 14 wherein the attenuated recombinant rabies virus contains one or more mutations in the rabies glycoprotein gene which confers attenuation of pathogenicity.

\* \* \* \* \*

```
                              SEQUENCE LISTING

<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Chemically synthesized primer for amplification
      of rabies virus glycoprotein gene

<400> SEQUENCE: 1
cgatgtatac gtacgaagat gttcctcagc tctcctg                              37

<210> SEQ ID NO 2
<211> LENGTH: 41
<212> TYPE: DNA
<213> ORGANISM: Artificial Sequence
<220> FEATURE:
<223> OTHER INFORMATION: Chemically synthesized primer for amplification
      of rabies virus glycoprotein gene

<400> SEQUENCE: 2
cttatcagct agctagctag ttacagtctg tctcaccccc a                         41

<210> SEQ ID NO 3
<211> LENGTH: 27
<212> TYPE: DNA
<213> ORGANISM: Artificial Sequence
<220> FEATURE:
<223> OTHER INFORMATION: Chemically synthesized primer for amplification
      of rabies virus glycoprotein gene

<400> SEQUENCE: 3
aacatgttat ggtgccatta aaccgct                                         27

<210> SEQ ID NO 4
<211> LENGTH: 27
<212> TYPE: DNA
<213> ORGANISM: Artificial Sequence
<220> FEATURE:
<223> OTHER INFORMATION: Chemically synthesized primer for amplification
      of rabies virus glycoprotein gene

<400> SEQUENCE: 4
gggtgttagt tttttcatg gacttgg                                          27

<210> SEQ ID NO 5
<211> LENGTH: 24
<212> TYPE: DNA
<213> ORGANISM: Artificial Sequence
<220> FEATURE:
<223> OTHER INFORMATION: Chemically synthesized primer for amplification
      of rabies virus glycoprotein gene

<400> SEQUENCE: 5
taattaacgt cctttcaacg atcc                                            24

<210> SEQ ID NO 6
<211> LENGTH: 28
<212> TYPE: DNA
<213> ORGANISM: Artificial Sequence
<220> FEATURE:
<223> OTHER INFORMATION: Chemically synthesized primer for amplification
``` of rabies virus glycoprotein gene

<400> SEQUENCE: 6
gagcatcttg aagtaagtag tctcaggt                                          28

<210> SEQ ID NO 7
<211> LENGTH: 50
<212> TYPE: DNA
<213> ORGANISM: Artificial Sequence
<220> FEATURE:
<223> OTHER INFORMATION: Chemically synthesized primer for amplification
      of a fragment of pSPBNGAS

<400> SEQUENCE: 7
cgatgtatac gtacgttttt gcgatcgccg tcctttcaac gatccaagtc                  50

<210> SEQ ID NO 8
<211> LENGTH: 49
<212> TYPE: DNA
<213> ORGANISM: Artificial Sequence
<220> FEATURE:
<223> OTHER INFORMATION: Chemically synthesized primer for amplification
      of a fragment of pSPBNGAS

<400> SEQUENCE: 8
cttagcgcta gcaaaaaggc gcgccggagg ggtgttagtt tttttcatg                   49

<210> SEQ ID NO 9
<211> LENGTH: 42
<212> TYPE: DNA
<213> ORGANISM: Artificial Sequence
<220> FEATURE:
<223> OTHER INFORMATION: Chemically synthesized primer for insertion of
      GAS gene into pSPBAANGAS

<400> SEQUENCE: 9
cgaatttatt ggcgcgccaa gatggttcct caggctctcc tg                          42

<210> SEQ ID NO 10
<211> LENGTH: 42
<212> TYPE: DNA
<213> ORGANISM: Artificial Sequence
<220> FEATURE:
<223> OTHER INFORMATION: Chemically synthesized primer for insertion of
      GAS gene into pSPBAANGAS

<400> SEQUENCE: 10
cttatcagct agctagctag ttacagtctg gtctcacccc ca                          42

<210> SEQ ID NO 11
<211> LENGTH: 50
<212> TYPE: DNA
<213> ORGANISM: Artificial Sequence
<220> FEATURE:
<223> OTHER INFORMATION: Chemically synthesized primer for amplification
      of rabies virus glycoprotein gene

<400> SEQUENCE: 11
ccggaattcc gtacgaagat gccggcagaa aacaagaaag ttagattcga                  50

<210> SEQ ID NO

-continued

```
<213> ORGANISM: Artificial Sequence
<220> FEATURE:
<223> OTHER INFORMATION: Chemically synthesized primer for amplification
      of rabies virus glycoprotein gene

<400> SEQUENCE: 12
tgctctagag cgatcgccgt ttatgtacat tgctctggta tcttaacc              48
```